(12) United States Patent
Ridley et al.

(10) Patent No.: US 8,496,592 B2
(45) Date of Patent: Jul. 30, 2013

(54) CLAMP FOR A MEDICAL PROBE DEVICE

(76) Inventors: Stephen F. Ridley, Columbia, SC (US);
M. Dexter Hagy, Greenville, SC (US);
David George Reed, Langhorne, PA (US); Craig A. Hidalgo, Langhorne, PA (US)

( * ) Notice: Subject to any disclaimer, the term of this patent is extended or adjusted under 35 U.S.C. 154(b) by 964 days.

(21) Appl. No.: 12/576,498

(22) Filed: Oct. 9, 2009

(65) Prior Publication Data
US 2011/0087106 A1  Apr. 14, 2011

(51) Int. Cl.
*A61B 8/14* (2006.01)
(52) U.S. Cl.
USPC ........... 600/459; 600/407; 600/437; 600/443; 600/461
(58) Field of Classification Search
USPC ........................ 600/407, 437, 459, 461, 443
See application file for complete search history.

(56) References Cited

U.S. PATENT DOCUMENTS

| | | | |
|---|---|---|---|
| 3,721,227 A | 3/1973 | Larson et al. |
| 4,108,165 A | 8/1978 | Kopp et al. |
| 4,407,294 A | 10/1983 | Vilkomerson |
| 4,608,989 A | 9/1986 | Drue et al. |
| 4,635,644 A | 1/1987 | Yagata |
| 4,671,292 A | 6/1987 | Matzuk |
| 5,078,144 A | 1/1992 | Sekino et al. |
| 5,329,927 A | 7/1994 | Gardineer et al. |
| 5,427,108 A | 6/1995 | Bollinger |
| 5,494,039 A | 2/1996 | Onik et al. |
| 5,758,650 A | 6/1998 | Miller et al. |
| 5,871,448 A | 2/1999 | Ellard |
| 5,924,992 A | 7/1999 | Park et al. |
| 5,928,219 A | 7/1999 | Friend et al. |
| 5,941,889 A | 8/1999 | Cermak |
| 6,138,495 A | 10/2000 | Paltieli et al. |
| 6,296,614 B1 | 10/2001 | Pruter |
| 6,361,499 B1 | 3/2002 | Bates et al. |
| 6,379,307 B1 | 4/2002 | Filly et al. |
| 6,475,152 B1 | 11/2002 | Kelly, Jr. et al. |
| 6,758,817 B1 | 7/2004 | Pruter et al. |
| 6,785,571 B2 | 8/2004 | Glossop |
| 7,241,267 B2 | 7/2007 | Furia |

(Continued)

FOREIGN PATENT DOCUMENTS

EP    0617922   10/1994
EP    0102800   3/2008

(Continued)

OTHER PUBLICATIONS

International Search Report for Appl. No. PCT/US2010/046751.

(Continued)

*Primary Examiner* — Unsu Jung
*Assistant Examiner* — Joel Lamprecht
(74) *Attorney, Agent, or Firm* — Dority & Manning PA

(57) ABSTRACT

Disclosed are medical probe devices and methods for use guiding of percutaneous probes during medical procedures. The probe devices include a clamp that can secure a probe at a targeted location. The devices can be utilized to guide a probe through the probe guide to a percutaneous target. Disclosed clamps can be utilized on probe devices incorporating an ultrasound transducer. In addition, the devices can include a sterilizable shield including a sterile probe guide for use in procedures requiring a sterile field. The sterilizable shield can be a single-use shield that can prevent contamination and re-use of the shield. The devices can define a beneficial geometry conducive to use by a single operator that can be utilized for percutaneous targets near the skin surface.

39 Claims, 20 Drawing Sheets

U.S. PATENT DOCUMENTS

| | | |
|---|---|---|
| 7,244,234 B2 | 7/2007 | Ridley et al. |
| 7,452,331 B1 | 11/2008 | Pruter |
| 2002/0123689 A1 | 9/2002 | Furia |
| 2003/0036709 A1 | 2/2003 | Jordan, III |
| 2003/0163142 A1 | 8/2003 | Paltieli et al. |
| 2003/0171681 A1 | 9/2003 | Weilandt |
| 2003/0233046 A1 | 12/2003 | Ferguson et al. |
| 2005/0234476 A1 | 10/2005 | Whitmore, III et al. |
| 2007/0073155 A1 | 3/2007 | Park et al. |
| 2007/0078346 A1 | 4/2007 | Park et al. |
| 2007/0149878 A1 | 6/2007 | Hankins |
| 2007/0208255 A1 | 9/2007 | Ridley et al. |
| 2008/0064960 A1 | 3/2008 | Whitmore, III et al. |
| 2008/0071215 A1 | 3/2008 | Woods et al. |
| 2008/0214925 A1 | 9/2008 | Wilson et al. |
| 2009/0143684 A1 | 6/2009 | Cermak et al. |

FOREIGN PATENT DOCUMENTS

| | | |
|---|---|---|
| JP | 56-43941 | 4/1981 |
| JP | 57-122861 | 7/1982 |
| JP | 59-007919 | 1/1984 |
| JP | 63-195803 | 12/1988 |
| JP | 1-110707 | 7/1989 |
| JP | 06-205776 | 7/1994 |
| JP | 7-506997 | 8/1995 |
| JP | 08-000614 | 1/1996 |
| JP | 08-229042 | 9/1996 |
| JP | 10-57376 | 3/1998 |
| JP | 2002-112998 | 4/2002 |
| JP | 09-322880 | 12/2007 |
| WO | WO 00/40155 | 7/2000 |
| WO | WO 00/57767 | 10/2000 |
| WO | WO 00/63658 | 10/2000 |
| WO | WO 2007/027470 | 3/2007 |

OTHER PUBLICATIONS

JP App. No. 2006539726 Office Action dated Jun. 1, 2010.
JP App. No. 2006539726 Office Action dated Sep. 28, 2010.
Product Data from Ascension Technology Corporation—3D Guidance medSAFE™, Jan. 2009, 3 pages.
Product Information for Civco Medical Solutions and Ascension Technology Corporation, Nov. 26, 2008, 8 pages.

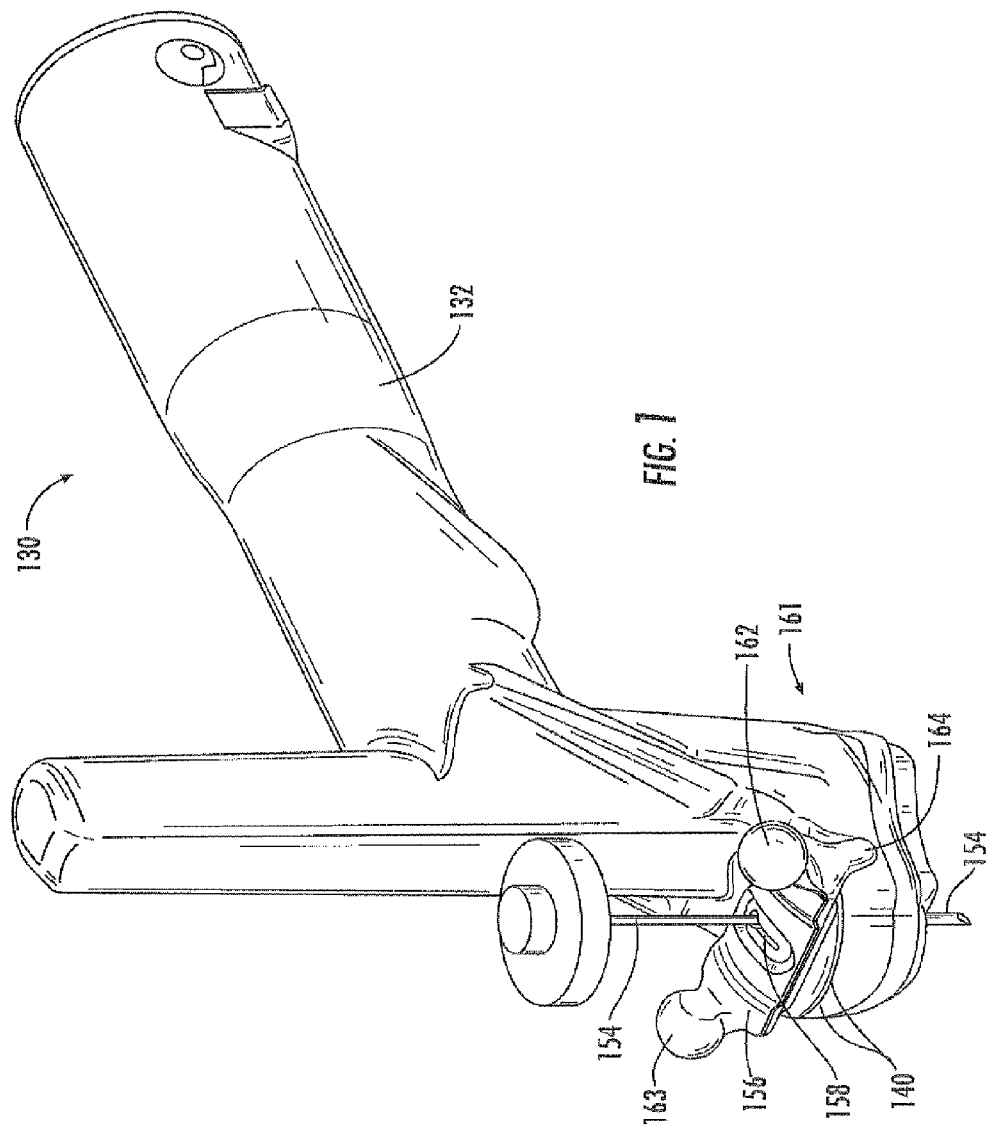

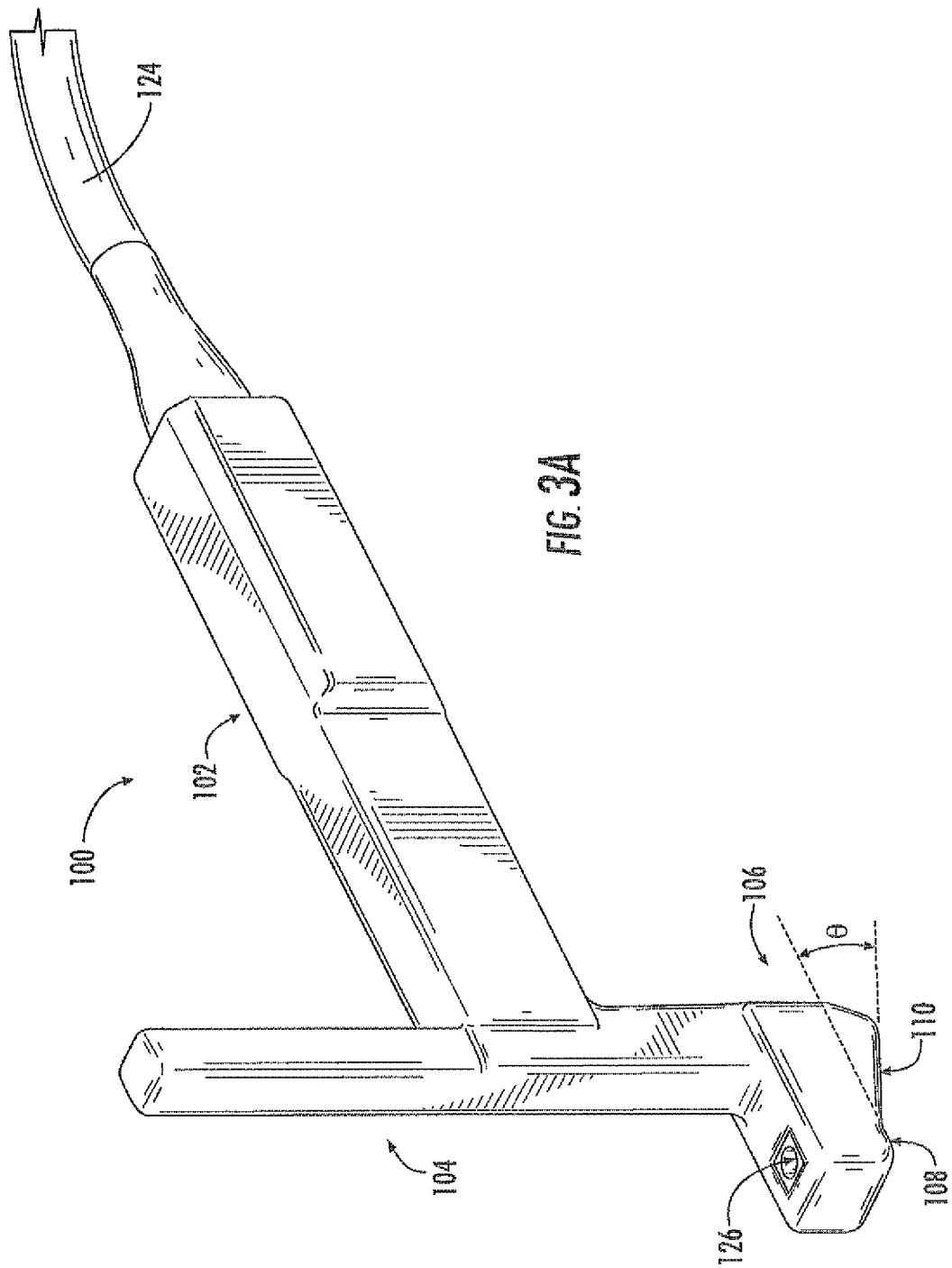

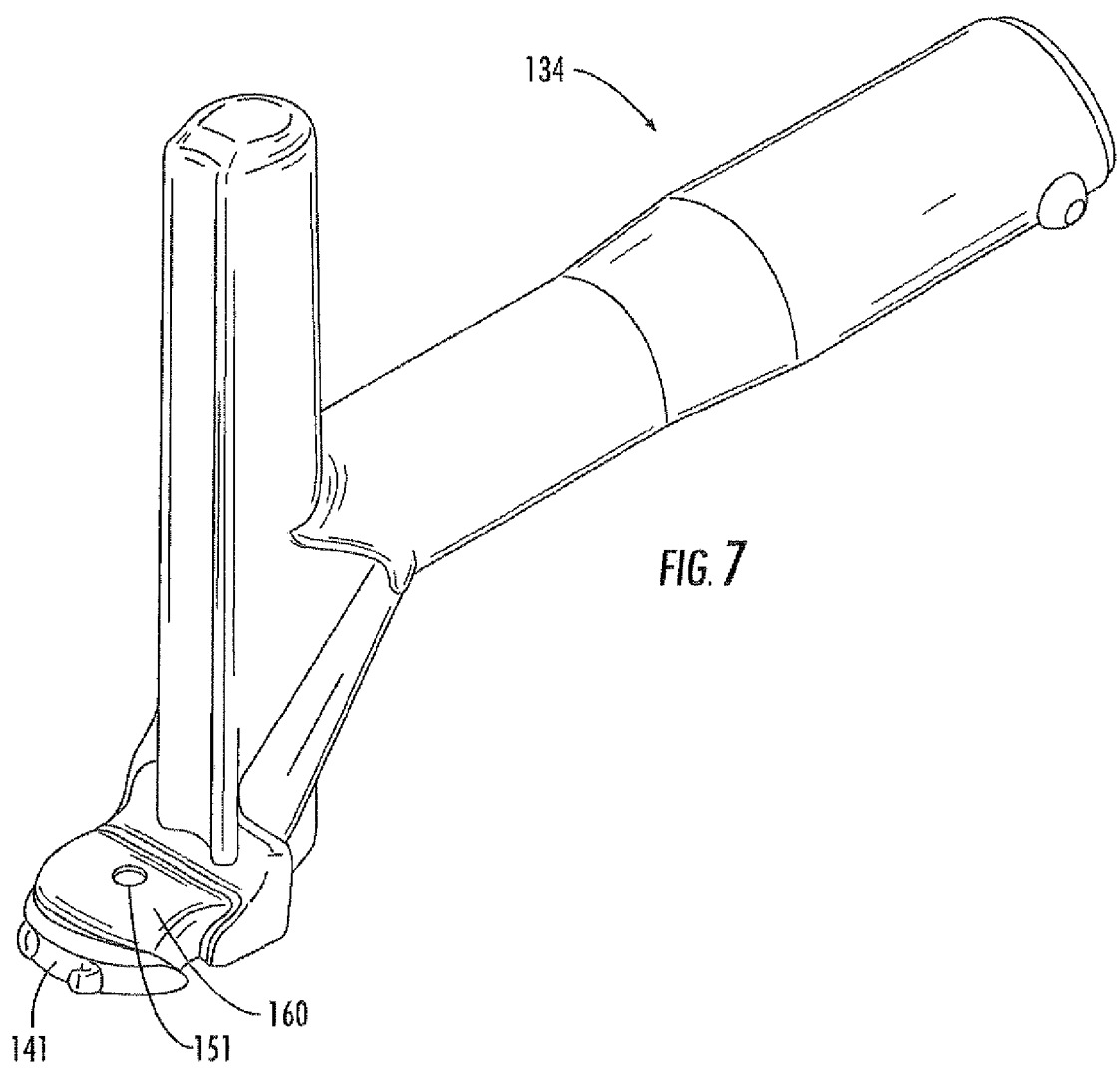

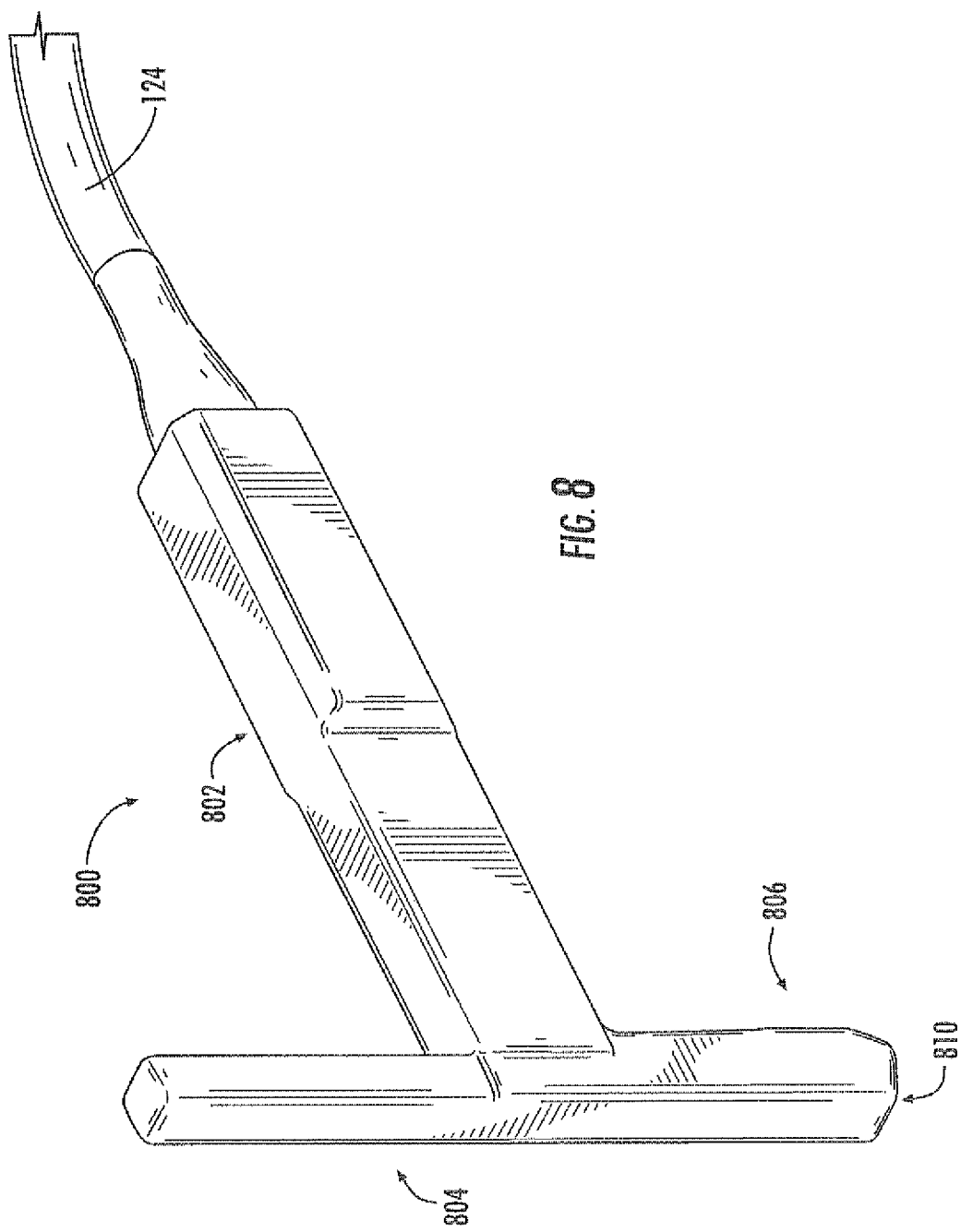

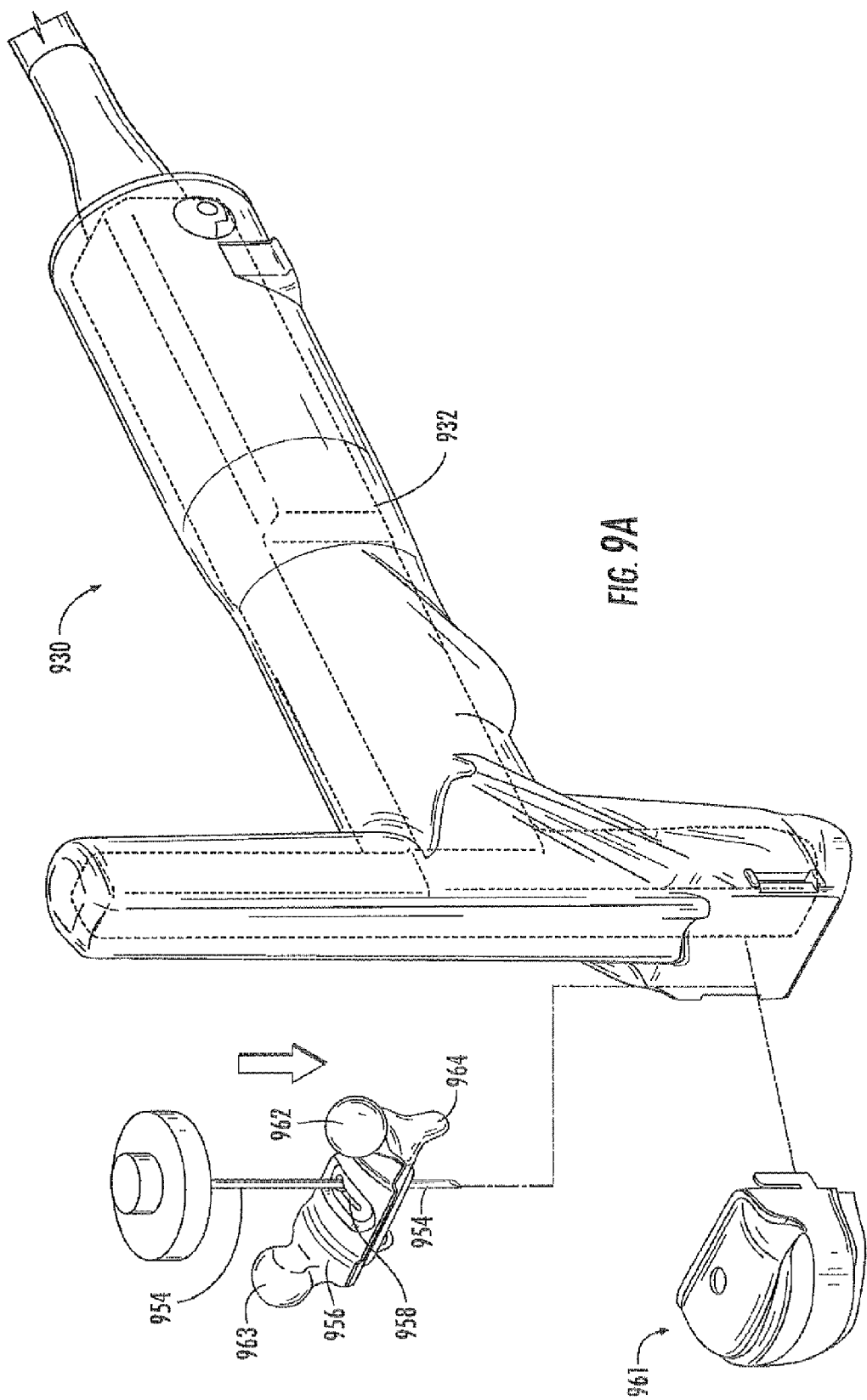

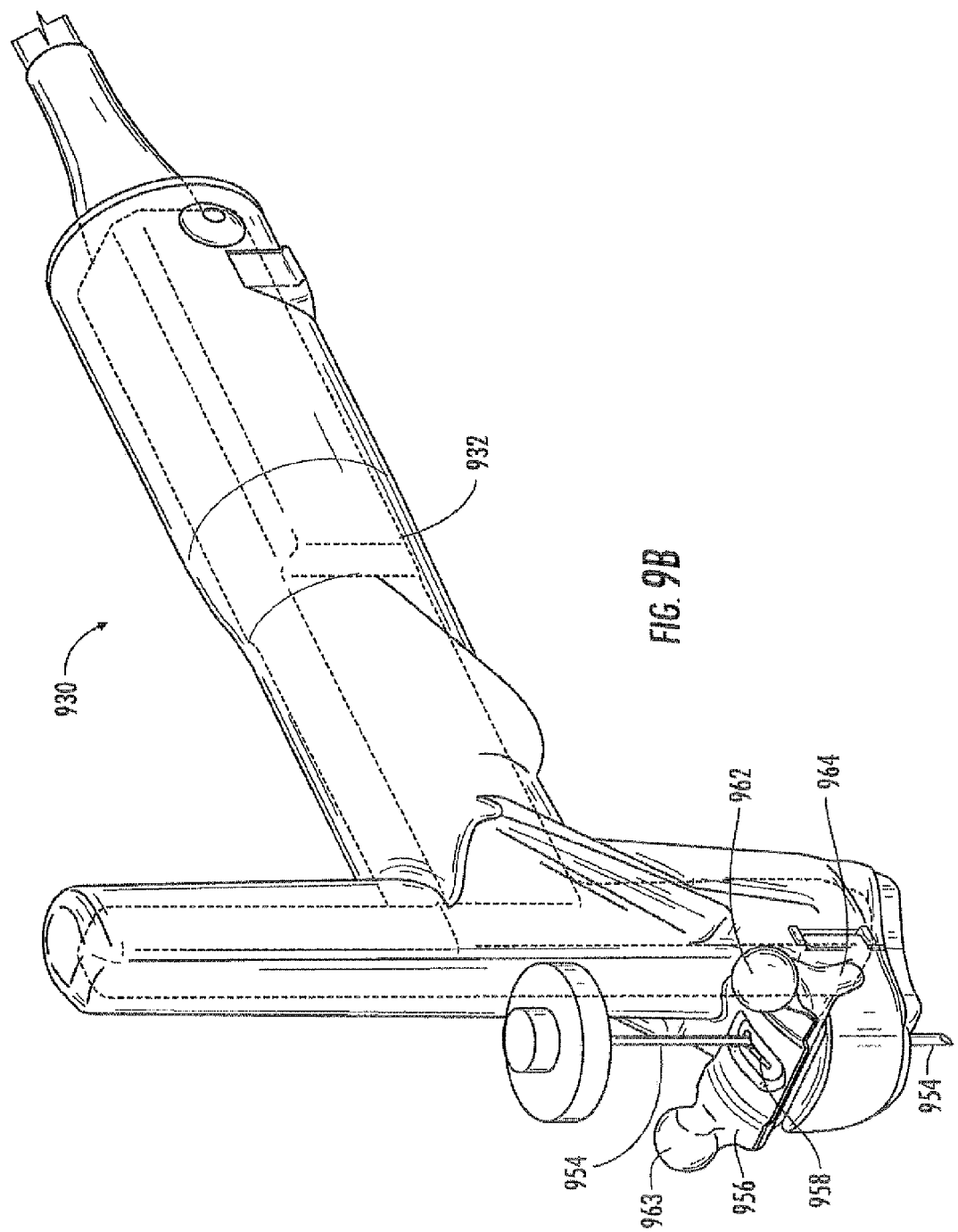

CLAMP FOR A MEDICAL PROBE DEVICE

BACKGROUND OF THE INVENTION

Medical probe devices are utilized for many purposes, chief of which include catheterization, centesis, and biopsy procedures. Percutaneous placement of probes using these devices is often performed with techniques which rely on ascertaining the correct locations of palpable or visible structures. This is neither a simple nor a risk-free procedure. For instance, proper insertion and placement of a percutaneous probe depends on correct localization of anatomical landmarks, proper positioning of the patient in relation to the care provider, and awareness of both the target's depth and angle from the point of probe insertion. Risks of unsuccessful placement of a probe can range from minor complications, such as patient anxiety and discomfort due to repetition of the procedure following incorrect initial placement, to severe complications, such as pneumothorax, arterial or venous laceration, or delay of delivery of life-saving fluids or medications in an emergency situation.

To improve proper placement of percutaneous probes, probe devices such as ultrasound transducers are often utilized. Ultrasound guided techniques often utilize two people, an ultrasound operator who locates the internal target and keeps an image of the target centrally located on a monitor, and a care provider who attempts to guide the probe to the target based upon the sonogram. Such techniques are very difficult perceptually, but have greatly improved the ability to properly place a percutaneous probe.

Even following proper placement of a probe, procedures can be complicated if the probe moves from the point of initial placement. For instance, during the Seldinger technique common for central venous catheter placement, a cannulated needle attached to a syringe is first guided into a vein. After the needle tip is in the lumen of the vein, the needle is held in place while a guide wire is fed down through the needle and into the vein. During this process, only a slight movement of the needle can cause the needle tip to move out of the vein, and the entire procedure must be repeated.

What are needed in the art are improved probe devices and methods for using same. For instance, what are needed in the art are probe devices that can be used to guide a probe to a percutaneous target and secure the probe in place following delivery to the target.

SUMMARY OF THE INVENTION

According to one embodiment, disclosed herein is a medical probe device defining a probe guide. The probe guide defines a longitudinal axis and provides an unimpeded passageway through the probe device for passage of a probe therethrough. A medical probe device as disclosed herein also includes a clamp. A clamp can define a clamping surface. During use, at least a portion of the clamp can be moved from a first position to a second position, and specifically, over that portion of the device including the probe guide. As this clamp portion is moved from the first position to the second position, at least a second portion of the clamp will pass the longitudinal axis of the probe guide. When the clamp is in the first position, a probe can be free to move in the probe guide and when the clamp is in the second position, a clamping surface can contact a probe held in the probe guide. At this second position, the probe can be tightly held by the clamp and prevented from moving in the probe guide. For example, in one embodiment the clamping surfaces can be opposing surfaces of an aperture formed in the clamp and a probe can be tightly held between the two clamping surfaces.

The clamp can be selectively moved by any means, e.g., it can pivot about an axis or can slide laterally over a surface to move from the first position to the second position. In one embodiment, an aperture that narrows in width from the first end to the second end can define the clamping surface. The probe device can also include a formation, e.g., a projection, an indentation, an area with a different surface tactility, or the like for a user to move the clamp from the first position to the second position.

A medical probe device can include other beneficial aspects as well. For instance, a medical probe device can incorporate an ultrasound transducer. In one preferred embodiment, the ultrasound transducer and the probe guide can be aligned. For example, the two can be aligned such that the path of a probe that passes through a probe guide can be within the scanned plane of a sonogram formed by the ultrasound device. Alternatively, the path of the probe guide can be out of the scanned plane, or at an angle convergent with the scanned plane.

In one embodiment, the medical probe device can include multiple separable pieces. For instance, a portion of the probe device defining the probe guide can be separably attachable to a clamp. Similarly, a portion of the probe device defining the probe guide can be separably attachable to, i.e., removably cooperable with, a portion of the device that can include an ultrasound transducer.

In one embodiment, a probe device can include an ultrasound transducer and a sterilizable shield that is removably cooperable with the ultrasound transducer housing. For instance, the clamp can be on the shield and the ultrasound transducer housing can be enclosed within the shield. In another embodiment, the clamp can be on a separable portion of the device that is directly or indirectly removably attachable to a sterilizable shield, and the sterilizable shield can enclose all or a portion of the ultrasound transducer. For example, a sterilizable shield can include a first section, a second section, and a fastener for connecting the first section and the second section to one another. Optionally, the fastener can be a single-use fastener that can be permanently disabled upon disconnection and separation of the first section and the second section from one another. In another embodiment, a sterilizable shield can be or can include a unitary, pliable material that can be formed around all or a portion of an ultrasound transducer.

A medical probe device can also include a visualization system. For instance, the ultrasound transducer can be connectable to a monitor for displaying a sonogram and the device can include a detector for detecting motion of a probe within the probe guide, the detector being in communication with a processing unit for displaying information concerning the motion of a probe in the probe guide. For example, the processing unit can display the probe and/or artifacts of the probe as it approaches a percutaneous target on a monitor or alternatively can display a computer generated image of a virtual probe on a monitor.

During use, a clamping surface can push against a probe to hold it in place. For instance a clamping surface can deform around a portion of the probe in an embodiment in which the portion of the clamp forming the clamping surface is formed of a soft material. Alternatively, an edge of a clamping surface can cut into the side of the probe in an embodiment in which the portion of the clamp forming the clamping surface is formed of a material that is harder than that of the probe.

Disclosed devices can be conveniently utilized by a single operator, for instance, in an ultrasound guided technique to deliver a probe to the lumen of a blood vessel.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1 illustrates one embodiment of a probe device including a clamp as disclosed herein.

FIG. 3A illustrates one embodiment of an ultrasound transducer housing as may be incorporated in a probe device as disclosed herein.

FIG. 7 illustrates the upper section of a probe device, the lower section of which is illustrated in FIG. 6.

FIG. 8 illustrates an ultrasound transducer housing that can be removably attachable to a portion of a probe device defining a probe guide.

FIGS. 9A and 9B illustrate a probe device including the ultrasound transducer housing of FIG. 8 enclosed in a sterilizable shield, a separable portion removably attachable thereto that defines a probe guide, and a clamp removably attachable thereto, with FIG. 9A showing the sections removed from one another and FIG. 9B showing the sections when attached together.

Figure 2A:
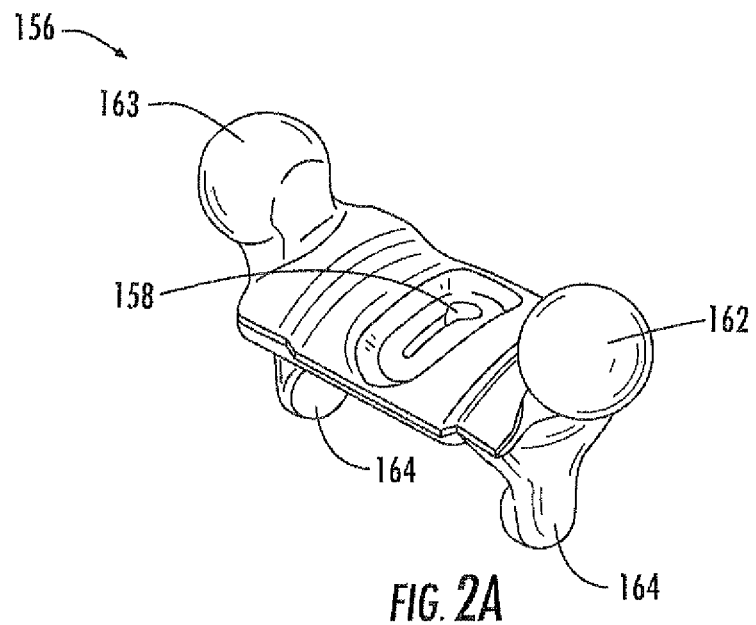
FIGS. 2A and 2B illustrate two views of the clamp of the probe device of FIG. 1.

Repeat use of reference characters in the present specification and drawings is intended to represent the same or analogous features of elements of the disclosed subject matter. Other objects, features and aspects of the subject matter are disclosed in or are obvious from the following detailed description.

DETAILED DESCRIPTION OF PREFERRED EMBODIMENTS

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

DEFINITIONS

As utilized herein, the term "probe" generally refers to a device that can be guided to a percutaneous location, for instance for delivery of a therapeutic, e.g., a compound or a treatment, to the location; for removal of material from the location; and so forth. For example, the term "probe" can refer to a needle, a tube, a biopsy device, or any other item that can be guided to a percutaneous location. In general, a probe can be guided by and used in conjunction with an ultrasound device as described herein.

As utilized herein, the term "probe device" generally refers to a device that can be utilized in conjunction with a probe, but does not necessarily include the probe itself.

DETAILED DESCRIPTION

According to one embodiment, disclosed herein are devices and methods for use in clamping a percutaneous probe during a medical procedure. More specifically, disclosed herein are probe devices that can include a clamp for securing a probe within the probe guide of the probe device. Devices can be conveniently held by an operator and can define an opening to accommodate a probe therethrough. In one embodiment, disclosed devices can include a visualization system so as to provide a real-time image of a percutaneous location on a sonogram and improve delivery of a probe to the percutaneous target.

Also disclosed herein is a probe device including a clamp in which the probe device can incorporate an ultrasound transducer in a housing. Moreover, a probe device can include a sterilizable shield that can surround all or a portion of an ultrasound transducer housing. Accordingly, disclosed probe devices can be utilized in one preferred embodiment in an ultrasound guided medical procedure that requires a sterile field to ensure the safety of a patient. For instance, disclosed devices can be used in a central venous catheterization procedure, in a biopsy procedure, and the like.

Beneficially, disclosed devices can be formed so as to be conveniently utilized by a single operator who can deliver a probe using the probe guidance system, clamp the probe in the device, and, in certain embodiments, also control an ultrasound transducer. Disclosed devices can include a variety of other beneficial features as well. For example, features of disclosed devices can improve contact between a skin surface and the surface of a device, can increase the effective field of the sonogram formed with an ultrasound transducer, and can prevent non-sterile use of a sterilizable shield of a device, all of which are described in greater detail herein.

In one preferred embodiment, disclosed devices can incorporate a system that can be used to visualize a percutaneous probe as it is being guided with a device. One preferred embodiment of a visualization system as may be incorporated with disclosed devices has been described in U.S. Pat. No. 7,244,234 to Ridley, et al., which is incorporated herein by reference. Through utilization of a visualization system, the path of a probe guided with a device and hence the location of the probe tip can be more clearly known in relation to a target imaged by an ultrasound device.

In accord with the present disclosure, one embodiment of a probe device including a clamp is illustrated in FIG. 1. Probe device 130 includes a clamp 156 that can firmly hold probe 154 in the probe device and prevent motion of the probe during a procedure such as a catheter insertion, a biopsy procedure, fluid aspiration, or the like. Motion of the percutaneous probe tip can be much less likely when the probe 154 is securely clamped to the probe device 130 and the probe device 130 is in turn held and stabilized by an operator as compared to devices in which a probe is simply held freehand by an operator.

A probe device 130 can be, in one embodiment, of a unitary construction and can be formed of a number of different biocompatible materials. For instance, a probe device 130 can be injection or blow molded from a polymeric material including, without limitation, polystyrene, polyethylene, polymethylpentene (TPX), polypropylene, polyurethane, polyvinyl chloride, and so forth.

As can be seen in FIG. 1, a probe 154 can extend through a probe guide (not shown) of probe device 130. Clamp 156 sits atop the base 161 of probe device 130 such that probe 154 passes through clamp aperture 158 as shown.

Figure 2B:
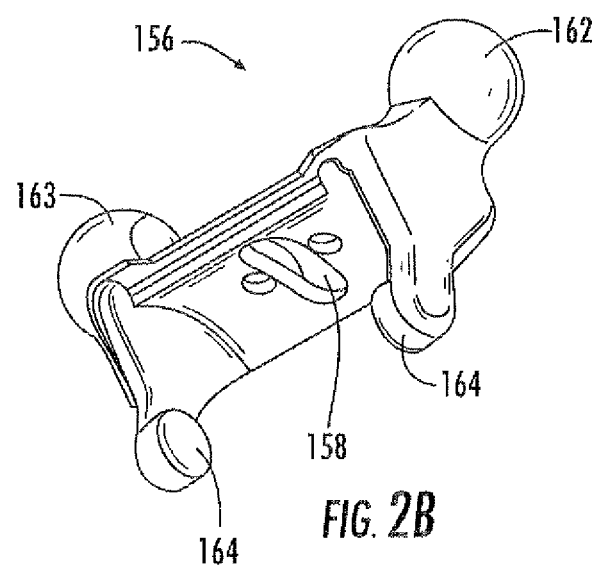

Additional details of clamp 156 can be seen with reference to FIGS. 2A and 2B. Aperture 158 includes a wide portion and a narrow portion, as shown. The wide portion can be of a size such that a probe can pass freely through the wide portion without hindrance. The narrow portion of aperture 158 can gradually narrow from the wide portion of the aperture to the tip of the aperture. Thus, when a probe is located in the aperture, and specifically at the wide portion of aperture 158, the probe is free to move in the probe guide. The clamp 156 can be moved in relation to a probe such that the clamping portion of the clamp crosses the axis of the probe and the clamping surface, e.g., a surface of the clamp that is adjacent a probe held in the probe guide of the device, can contact the probe. In this illustrated case, the clamping surface is the inner surface of the aperture 158. As the clamp portion is moved past the probe, the clamping surface at the narrow end of aperture 158 can contact the probe and the probe can become tightly trapped in the narrow portion of the aperture 158 as the width of aperture 158 decreases.

In another embodiment, rather than trapping a probe between two clamping surfaces of a clamp, as is the case with the clamp illustrated in FIG. 2, a single clamping surface can contact a probe. For instance, a clamping surface can force a probe against the wall of the probe guide to secure the probe in place. For example, a clamp can include a single clamping surface that can be geometrically arranged so as to be set an angle with reference to the probe guide of a device. Thus, as the clamp portion crosses the probe guide axis, the probe held in the probe guide contacts the clamping surface and becomes pressed against the wall of the probe guide by the force of the single clamping surface and can be firmly gripped between the side of the aperture and the clamping surface of the probe guide. In such an embodiment, the clamping surface of the clamp need not be one side of an aperture defined by the clamp, but may be, by way of example, an outer edge of a clamp section, with no opposing piece on the clamp.

A clamp as disclosed herein can be formed of any biocompatible material. In one preferred embodiment, the material forming the clamp can also be sterilizable. Referring again to FIG. 2, in one embodiment, at least that portion of a clamp 156 that defines the clamping surface, e.g., aperture 158, can be formed of a hard material, for example a hard polymer or a stainless steel. In particular, this portion of clamp 156 can be formed of a material that is harder than a probe to be held by the clamp. In this embodiment, the clamping surface can cut into the surface of a probe, providing additional holding power, that can add to the friction hold provided by trapping the clamp against the clamping surface, e.g., in the narrow portion of aperture 158.

In another embodiment a clamp, and particularly that portion of a clamp 156 defining the clamping surface(s), e.g., aperture 158, can be formed of a material that is softer than a probe to be held in the clamp. For example, a clamp can be formed of a relatively soft material, e.g., a soft polyurethane or other biocompatible polymeric material. In this embodiment, the clamping surface(s) can deform somewhat as a probe is forced against the clamping surface. The deformation of a clamping surface about a probe can increase the grip on the probe, more securely holding the probe in place in the clamp.

A clamp can define additional features that can improve its holding ability. For instance, a clamping surface can define a series of serrations. Upon contact with the probe, the serrations of the clamping surface(s) can provide increased surface area for contact between the clamp and the probe, improving hold between the two. Moreover, in those embodiments in which the material forming the clamping surface(s) is harder than that of the probe, serrations on the clamping surface can cut into the surface of the probe at the points of contact, further improving hold between the two.

Referring again to FIG. 2A, Clamp 156 includes two formations 162, 163 that can be used to move clamp 156 and trap probe 154 in the aperture 158 as previously discussed. For example, a probe device 130 can be held against the skin surface of a subject and the user can move the clamp 156 by use of formation 162 or formation 163 with his/her thumb to force the probe into the narrow section of aperture 158 and firmly clamp the probe 154 in place.

In the illustrated embodiment, clamp 156 includes two formations 162, 163, one on either side of clamp 156 such that the clamp can be operated while held in either the right or left hand of a user. In other embodiments, clamp 156 can include only a single formation, for instance in those embodiments in which a probe device is designed for only right-handed or left-handed use, or alternatively, when the single formation can be accessed from either side of the device. Moreover, the shape of the formations 162, 163 can be any shape that can be accessed by a user and can be pushed, pulled, twisted or otherwise activated to move a clamp and tightly grip a probe in a probe guide. For example a formation can be round, as illustrated, or can be a flat, paddle-shaped formation, a post, or any other convenient shape. Moreover, any shape or style of formation can be utilized to aid in moving the clamp to force a clamping surface against a probe. For instance, a clamp can define an indentation to be used in moving a clamp. In another embodiment, a clamp can define a rough tactility at a location that can aid in moving the clamp with a thumb or finger. Equivalent or alternative formations would be obvious to one of ordinary skill in the art.

Referring again to FIG. 1, clamp 156 is attached to probe device 130 at a pivot point. For instance, tabs 164 of clamp 156 can fit into recesses formed in probe device 130. During use, clamp 156 can rotate about the pivot point of tabs 164 and over the upper surface of base 161 of probe device 130.

The rotation of a clamp about a pivot to secure a probe is not a requirement of disclosed clamps. For example, in another embodiment, all or a portion of clamp can slide laterally across a surface of a probe device to clamp a probe in place. In general, any motion of all or a portion of a clamp that can be controlled by a user such that at least a portion of the clamp moves past a probe and can grip a probe as described is encompassed in the present disclosure.

When a probe is to be removed from a percutaneous location, or if during a procedure, a probe is to be moved from one percutaneous location to another, a formation can be utilized to move a clamping surface in the opposite direction as was used to clamp the probe, freeing the probe.

Figure 3B:
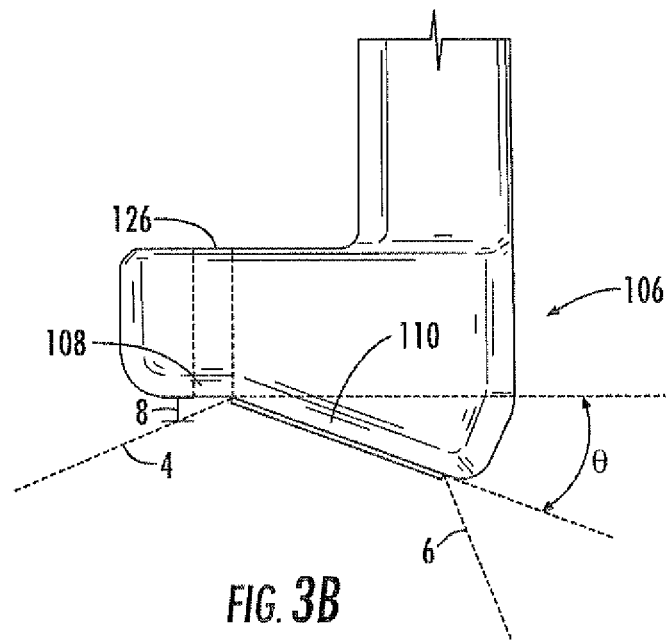
FIG. 3B illustrates the base of the ultrasound transducer housing of FIG. 3A.
Figure 4:
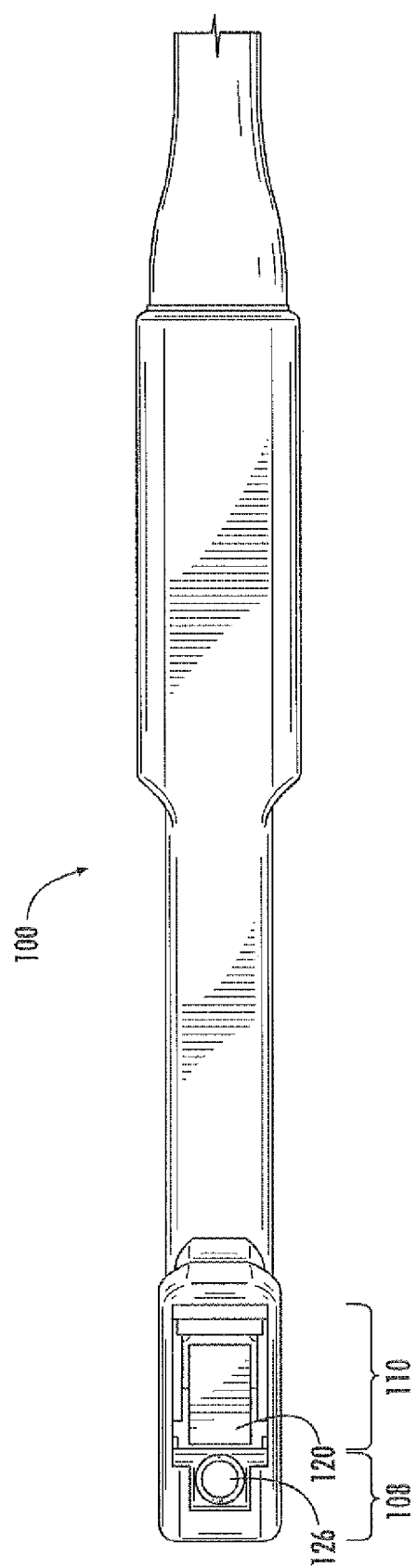
FIG. 4 illustrates a bottom view of the ultrasound transducer housing of FIG. 3A.

According to one embodiment, a probe device as disclosed herein can incorporate an ultrasound transducer. FIG. 3A illustrates one embodiment of an ultrasound transducer housing generally 100 as may be utilized as a probe device itself or alternatively incorporated as a portion of a probe device as disclosed herein. Transducer housing 100 includes handle 102, post 104, and base 106. FIG. 4 provides a bottom view of transducer housing 100. An ultrasound transducer 120 that transmits and receives ultrasonic waves can be located in base 106, as shown. Ultrasound transducer housing 100 can be formed of any suitable materials. For instance, any moldable polymeric material that can securely encase the ultrasound transducer 120 as well as contain associated electronics, wiring, switches, and the like and will not interfere with the functioning of the transducer 120 can be utilized.

Any type of ultrasound transducer as is generally known in the art can be incorporated in transducer housing 100. By way of example, a piezoelectric transducer formed of one or more piezoelectric crystalline materials arranged in a two or three-dimensional array can be utilized. Such materials generally include ferroelectric piezoceramic crystalline materials such as lead zirconate titanate (PZT). In one embodiment, the elements that form the array can be individual electrode or electrode segments mounted on a single piezoelectric substrate, such as those described in U.S. Pat. No. 5,291,090 to Dias, which is incorporated herein by reference thereto.

In general, an ultrasound transducer 120 can be formed of multiple elements. However, single crystal devices are also encompassed by the present disclosure. The use of a multiple element ultrasound transducer can be advantageous in certain embodiments, as the individual elements that make up the array can be controlled so as to limit or prevent any break or edge effects in the sonogram. For instance, the firing sequence of individual crystals can be manipulated through various control systems and prevent any possible 'blind spots' in a sonogram as well as to clarify the edges of individual biological structures in the sonogram. Such control systems are generally known in the art and thus will not be described in detail.

Ultrasound transducer housing 100 defines a probe guide opening 126 that passes through base 106. As can be seen in FIG. 4, probe guide opening 126 can be aligned with transducer 120. A probe that is guided through the probe guide opening 126 can travel on a path that is generally parallel to the scanned plane of a sonogram formed by use of the ultrasound device. In general, the scanned plane (i.e., the plane of the sonogram) is the geometric central plane of the beam transmitted from the ultrasound transducer 120. In one preferred embodiment, the path of a probe guided through probe guide opening 126 can be within the scanned plane. This is not a requirement of the present disclosure, however. For instance, the path of a probe passing through probe guide can be at an angle to the scanned plane such that it intersects the scanned plane at a point. By way of example, the line defined by the path of a probe passing through the probe guide can be at an angle of ±1° of the scanned plane in one embodiment, at an angle of ±0.6 degrees in another embodiment, or at a lesser or greater angle in another embodiment. For instance, a line defined by the path of a probe passing through the probe guide can be at an angle of ±10°, ±20°, ±45°, or even greater, in other embodiments.

Generally, ultrasound transducer 120 can be connected via signal wires in a cable 124 that leads to a processor that processes the data to form a sonogram on a monitor, as is generally known in the art. In the particular embodiment as illustrated in FIG. 3A, cable 124 is internal to handle 102 of the ultrasound transducer housing 100, though this particular arrangement is not a requirement of the disclosure. Handle 102 can generally be set at an angle to post 104 of transducer housing 100 so as to be comfortably held in the hand while the device is being utilized. For instance, in the illustrated embodiment, handle 102 is about 90° to post 104, though this angle can be varied as desired. Moreover, in another embodiment described further herein, a device need not include an extending handle portion at all.

Base 106 defines a lower surface 108 defining probe guide opening 126 and lower surface 110 including transducer 120. Surfaces 108 and 110 together can form a skin contacting surface on the base 106 of the device 100. As can be seen, surfaces 108 and 110 are contiguous and angled with respect to one another. The angle between surface 108 and 110 can vary, for instance in one embodiment the angle marked as $\theta$ in FIG. 3A can vary from 0 to about 30°, or from about 10° to about 20° in another embodiment. Accordingly, the angle between surfaces 108 and 110 can be greater than about 150° and less than 180° in one embodiment, or greater than about 160° and less than about 170° in another embodiment.

It has been found that such a geometry can be beneficial in certain embodiments. For instance, referring to FIG. 3B, base 106 is illustrated with the edges of a scanned plane formed by ultrasound transducer 120 shown within broken lines 4 and 6. The distance 8 from the termination of probe guide opening 126 to the edge 4 of the scanned plane is also shown. During use, the portion of base 106 including surface 110 can press into the skin of a subject somewhat and ensure good contact between the ultrasound transducer, ultrasonic gel, and the skin. Upon passing a probe through the probe guide opening 126, the probe will contact the skin and travel the short percutaneous distance 8 before entering the scanned plane. The distance 8 can depend upon the angle between the surfaces 108 and 110, and can be relatively small. For instance distance 8 can be less than about 25 mm, less than about 10 mm, less than about 5 mm or less than about 1 mm.

Figure 3C:
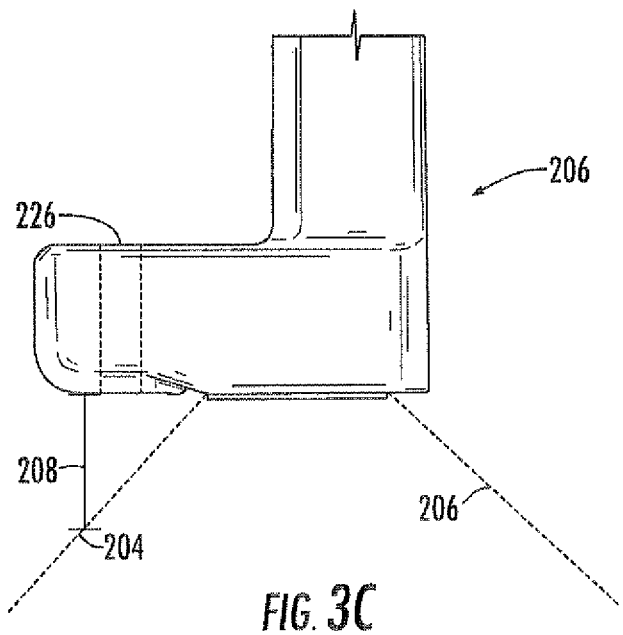
FIG. 3C illustrates the base of another ultrasound transducer housing as disclosed herein.

In comparison, FIG. 3C illustrates a base 206 in which the entire bottom edge of the base is planar, i.e., the skin contacting surface of the base does not include angled portions. FIG. 3C also illustrates the edges of a scanned plane formed by a transducer by use of broken lines 204 and 206. As can be seen, the distance 208 between the point a probe will exit probe guide opening 226 and enter the scanned plane at 204 is greater than the distance 8 in the embodiment in FIG. 3B. An embodiment including a base that defines an angled bottom surface, as is illustrated in FIG. 3B may be preferred in those embodiments in which a percutaneous target may be close to the skin surface.

It should also be understood that while the skin contacting surface and portions thereof of the illustrated probe devices are generally planar, this is not a requirement of the disclosed subject matter. For instance, with regard to FIG. 3B, surface 108 and/or surface 110 can be curved, e.g., can define an arcuate profile along either or both axes of the surface. In this embodiment, a curved surface can define a plane between the intersection line of two portions forming the skin contacting surface and a point at the outer edge of the curved surface. Planes defined by two intersecting curved skin contacting surfaces can correspond in a like manner to a planar skin contacting surface (or portions thereof) as described above.

It should be understood that any particular geometric configuration for transducer housing 100 and its individual sections is not essential to the present invention. For example, the base 106 of transducer housing 100 may be oblong, square, round, rectangular or any other suitable shape. In certain embodiments, the shape of ultrasound housing 100 may be particularly designed to fit specific locations of the anatomy. For example, ultrasound housing 100 may be shaped to be utilized specifically for infraclavicular approach to the subclavian vein, approach to the internal jugular vein, specific biopsy procedures including, without limitation, breast biopsy, thyroid nodule biopsy, prostate biopsy, lymph node biopsy, and so forth, or some other specific use. Variations in shape for any particular application can include, for example, a specific geometry for the footprint of base 106, alteration in the size of post 104 and/or handle 102, as well as variation in angles at which various elements of a device meet each other, such as the angle defined by the bottom of base 106 previously discussed. For example, the footprint of base 106 can be any suitable shape and size, e.g., rectangular, round, oblong, triangular, etc. By way of example, the skin contacting surface of base 106 can be between about 0.5 inches and about 6 inches on its greatest length. In one embodiment, the footprint of base 106 can be about 0.5 inches on its greatest width and can promote stability of the device during use. In other embodiments, it can be larger, however, such as about 1 inch on its greatest width, about 2 inches on its greatest width, or even larger.

Transducer housing 100 can be used as is, with no additional shield or covering over the housing 100. According to this embodiment, a probe, e.g., a needle, can pass through probe guide opening 126 and can be directed to a target that is visualized on a sonogram formed by use of ultrasound transducer 120. Following location of the probe at the target a clamp as described herein and located on the ultrasound transducer housing can clamp the probe in the probe guide of the ultrasound transducer housing 100.

A probe device can include an ultrasound transducer housing that can be utilized in conjunction with a sterilizable shield, for instance in those embodiments in which a probe is intended for use in a sterile field. According to this embodiment, a transducer housing can be utilized in conjunction with a sterilizable shield that can provide a sterile barrier between a patient and all or a portion of the ultrasound transducer housing during a medical procedure.

A sterilizable shield can be formed of sterilizable materials as are generally known in the art. In one embodiment, a sterilizable shield can be formed of single-use materials such as polymeric materials and the entire shield can be properly disposed of following a single use. In another embodiment, a sterilizable shield can be utilized multiple times, in which case it can be formed of a material that can be properly sterilized between uses. By way of example, a sterilizable shield can be formed of a moldable thermoplastic or thermoset polymeric material including, without limitation, polyester, polyvinyl chloride, polycarbonate, and so forth.

Figure 5:
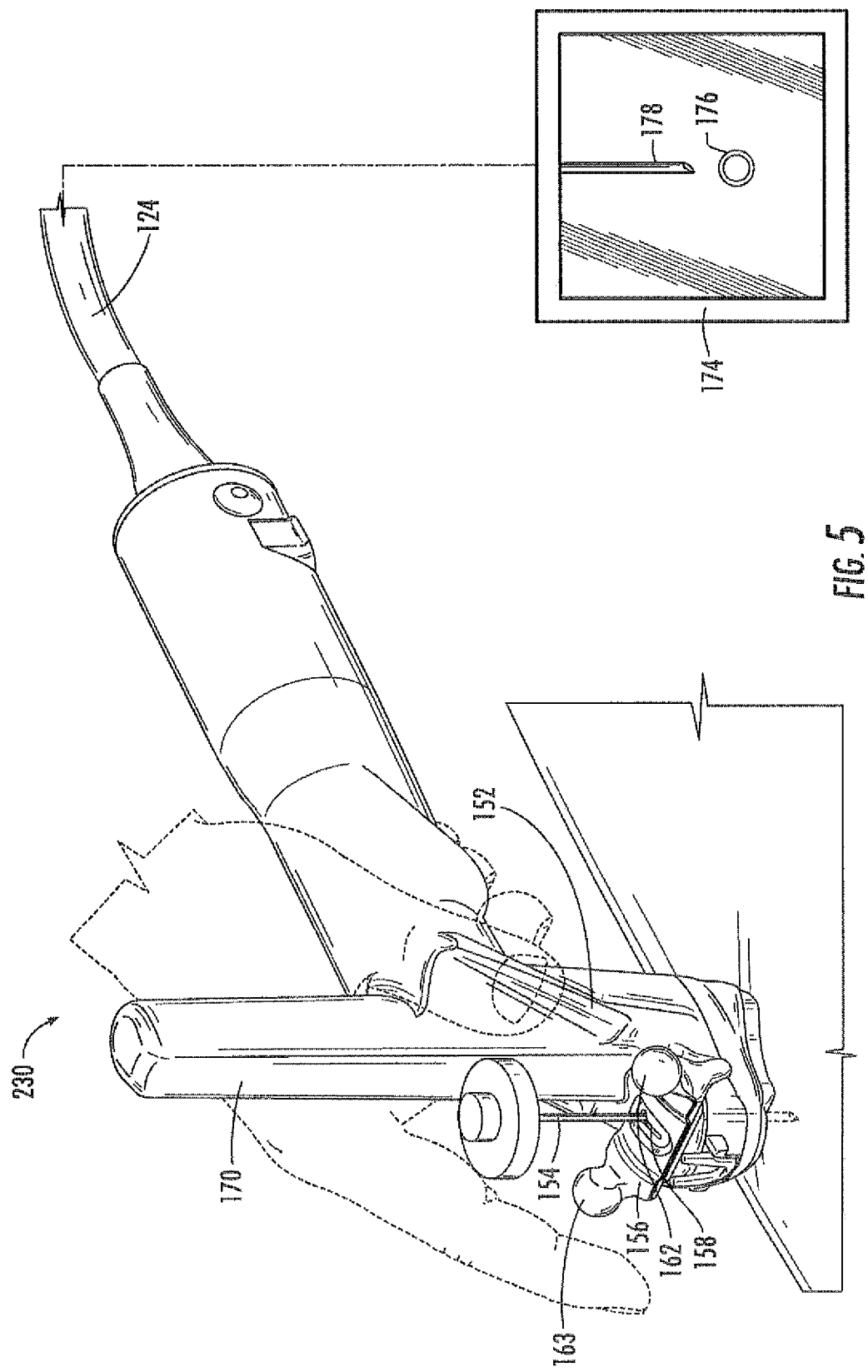
FIG. 5 illustrates one embodiment of a probe device including a sterilizable shield as disclosed herein.

FIG. 5 illustrates one example of a sterilizable shield 230 during use as may be utilized to encase ultrasound transducer housing 100 (not shown in FIG. 5). Sterilizable shield 230 can include a lower section 132, details of which are shown in FIG. 6, and an upper section 134, details of which are shown in FIG. 7.

Figure 6:
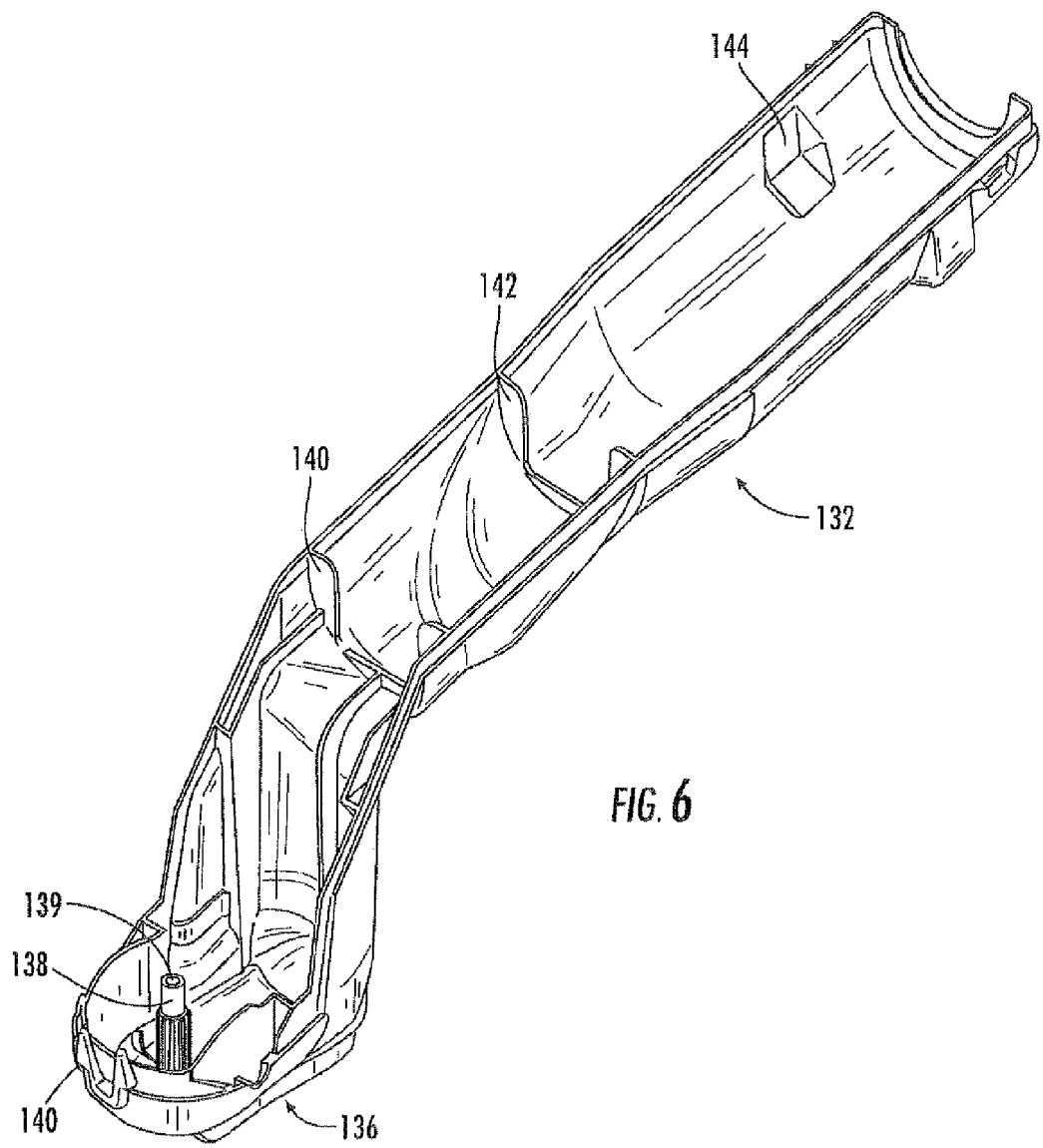
FIG. 6 illustrates a section of a probe device that can incorporate an ultrasound transducer housing as is illustrated in FIG. 3A.

With reference to FIG. 6, shield section 132 can include a base 136 formed of an ultrasonic transmissive material. Base 136 can be of any suitable size and shape, but formed such that the ultrasound transducer housing base may be seated firmly in shield base 136. Generally, a small amount of an ultrasonic gel can be placed between the bottom surface of the transducer housing base and shield base 136 during seating to prevent any air between the two and promote transmission of ultrasonic waves.

Arising out of shield base 136 is guide post 138. Guide post 138 defines at least a portion of a probe guide 139 therethrough. Probe guide 139 extends uninterrupted completely through both guide post 138 and shield base 136. Guide post 138 can include tabs as shown, or other formations such as hooks, insets, or the like that can be utilized to properly assemble shield base 136 about ultrasound transducer housing 100. In one embodiment, guide post 138 may include a removable cap (not shown) for protection of the interior sterile surface of probe guide 139 during assembly of shield 230 with an ultrasound transducer housing.

As can be seen, shield section 132 can also include tabs 140, 142, 144, etc. that can be utilized in properly seating an ultrasound housing within shield base 132 as well as aligning shield section 132 with shield section 134 when assembling the complete shield 230 about an ultrasound transducer housing.

In the illustrated embodiment, tabs 140 on shield base 132 match up with corresponding notch 141 on shield section 134 shown in FIG. 7. Together tabs 140 and notch 141 form a fastener that can secure shield section 132 and shield section 134 to one another. During assembly, tabs 140 can snap into notch 141 to securely fasten the two sections together and prevent separation of the sections 132, 134 during use. Of course, a shield can include additional fasteners at other locations between the two sections, or can include a single fastener at an alternative location, as would be known to one of skill in the art.

In order to disassemble shield 230, tabs 140 can be simply pinched together and slid out of notch 141. In another embodiment, a single-use fastening mechanism can be employed to secure sections of a sterilizable shield to one another. According to this embodiment, in order to disassemble a shield following use, the tabs of the fastener can be permanently disabled upon disassembly of the shield. For instance, tabs 140 and/or notch 141 can be permanently broken away from the shield by a pulling or twisting motion, allowing the shield sections to come apart and also ensuring that the shield, which is no longer sterile, cannot be utilized again. Any method that can ensure that a fastener can only be utilized a single time may alternatively be utilized.

Another beneficial feature of disclosed devices can be the geometry of the handle of a device. For instance, as previously mentioned with regard to the transducer housing, the angle at which a handle is placed on a probe device can be varied so as to obtain a more comfortable grip on the device while holding the transducer base tightly against the skin. Additional aspects of a handle can be improved as well. For example, as can be seen on FIG. 5 the handle of shield 230 can include a finger grip 152 that can improve the grip of a user on the device. In other embodiments additional finger grips can be included, as desired. For instance, in one embodiment finger grips can be provided on a handle such that the handle is specifically designed for left-handed or right-handed use.

Sterilizable shield 230 also includes section 134, illustrated in FIG. 7. Section 134 can be removably attached to section 132 to enclose an ultrasound transducer housing, e.g., ultrasound transducer housing 100, as previously discussed. Section 134 defines the terminal portion 151 of probe guide 139 shown in FIG. 6. Terminal portion 151 is sized so as to snugly reside over the top of guide post 138 of section 132 and form uninterrupted probe guide 139 extending from the top surface of portion 160 of section 134 to the bottom surface of base 136 of section 132.

To assemble the illustrated sterilizable probe device, ultrasound transducer housing 100 defining probe guide opening 126 shown in FIG. 3A can be seated in shield base 136 of section 132 such that guide post 138 extends through transducer housing probe guide opening 126. As probe guide opening 126 of transducer housing 100 is slid over guide post 138, tabs on guide post 138 can slide or snap into recesses of probe guide opening 126 (not shown), helping to properly seat transducer housing 100 in section 132. After ultrasound transducer housing 100 is seated in section 132, section 134 can be aligned with section 132 and fastened into place to cover the top of transducer housing 100. If a protective cap covers the end of guide post 138, it can be removed during assembly and maintain the sterility of the interior of the probe guide 139 throughout the assembly process. Tabs 140 can snap or slide into recesses notch 141 to fasten and secure section 132 and 134 together.

Following the above described assembly process, probe guide 139 can extend continuously from the top of portion 160 of shield portion 134 through the shield base 136. Moreover, and of great benefit to the device, probe guide 139 can be sterile and within the probe guide opening 126 of ultrasound transducer housing 100.

Though illustrated as being formed of two separable sections, a sterilizable shield as disclosed herein can be hinged or can include additional sections, as desired. For instance, a sterilizable shield can be formed of two, three, or more separable sections that can be assembled to enclose an ultrasound housing and form a sterile barrier between the enclosed housing and an exterior field. In another embodiment, a sterilizable shield can be of a unitary construction. For instance, a sterilizable shield can be of a pliant material that can enclose all or a portion of an ultrasound housing and form a sterile barrier between the enclosed housing and an exterior field.

FIG. 8 illustrates another embodiment of an ultrasound transducer housing 800 that can be removably attachable to a sterilizable shield. According to this embodiment, ultrasound transducer housing 800 can include a handle 802, a post 804, and a base 806. Ultrasound transducer housing 800 also defines a lower surface 810, as shown. In this particular embodiment, however, the ultrasound transducer housing does not include a probe guide opening. Instead, ultrasound transducer housing 800 is removably attachable to a second portion of a device that defines the probe guide opening and can be utilized in conjunction with a clamp. For instance, ultrasound transducer housing 800 can be utilized in conjunction with a sterilizable shield that defines the probe guide and clamp. Moreover, the sterilizable shield can be formed of a single or multiple removably attachable pieces.

FIGS. 9A and 9B illustrate one embodiment of a sterilizable shield that can be used in conjunction with an ultrasound device 800 illustrated in FIG. 8. With reference to FIG. 9A, sterilizable shield 930 that can enclose an ultrasound transducer housing 800. Sterilizable shield 930 can be formed of multiple attachable pieces. Specifically, sterilizable shield 930 includes section 932 and section 961 that defines a probe guide for passage of probe 954 therethrough. Additionally, section 932 can be separable into two or more section, as illustrated for device 230 of FIGS. 5-7. Section 961 can also include clamp 956 defining aperture 958 and formations 962, 963 that rotates about pivot 964 for clamping probe 954 in the probe guide. During use, section 961 can be attached to shield 932, for instance by use of aligned tabs and notches, and so forth, so as to attach the probe guide portion to the sterilizable shield, as shown in FIG. 9B.

Of course, any other arrangement of the individual portions of a device are encompassed within the present disclosure. For instance, in one embodiment, an ultrasound transducer housing that does not define a probe guide opening, as illustrated in FIG. 8, can be removably attached to a piece that can define a probe guide opening and include the clamp, without enclosing all or a portion of the ultrasound transducer housing in a shield. In another embodiment, a sterilizable shield portion can cover only the skin contacting surface of a device. For instance, a shield portion can snap onto the base of a device.

In yet another embodiment, a sterilizable shield can be a pliant material that can 'wrap' all or a portion of an ultrasound transducer housing. In this embodiment, a separable section that defines a probe guide opening and can include the clamp can be attached to the sterilizable shield either directly or indirectly. For instance feature(s) (e.g., clips, notches, etc.) that are a part of or attached to the ultrasound transducer housing can provide a site to which the separable section can attach. Upon attachment, the pliant sterilizable shield can then be held between the ultrasound transducer housing and the separable section.

Figure 10:
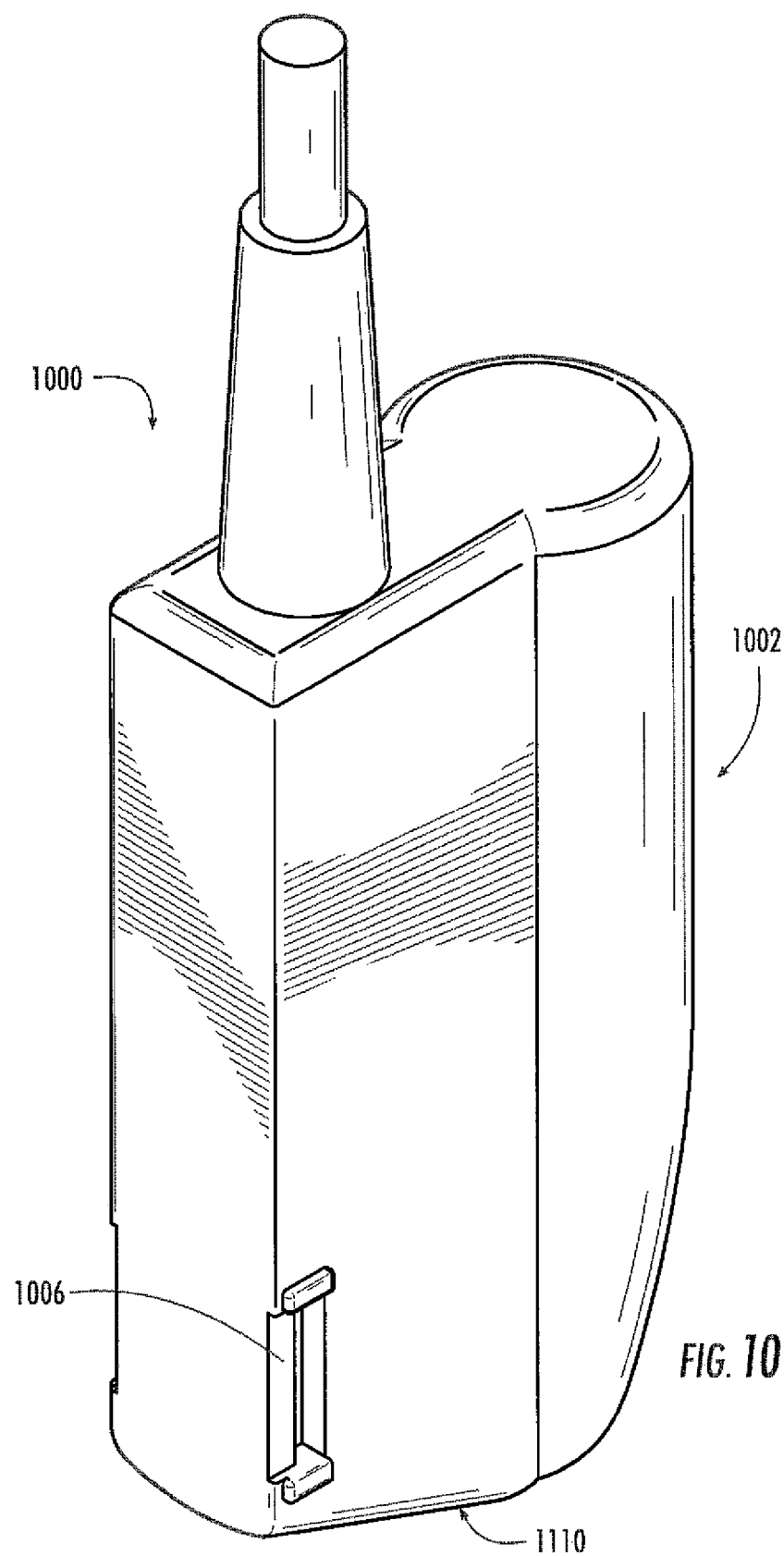
FIG. 10 illustrates another embodiment of a probe device as disclosed herein.
Figure 11:
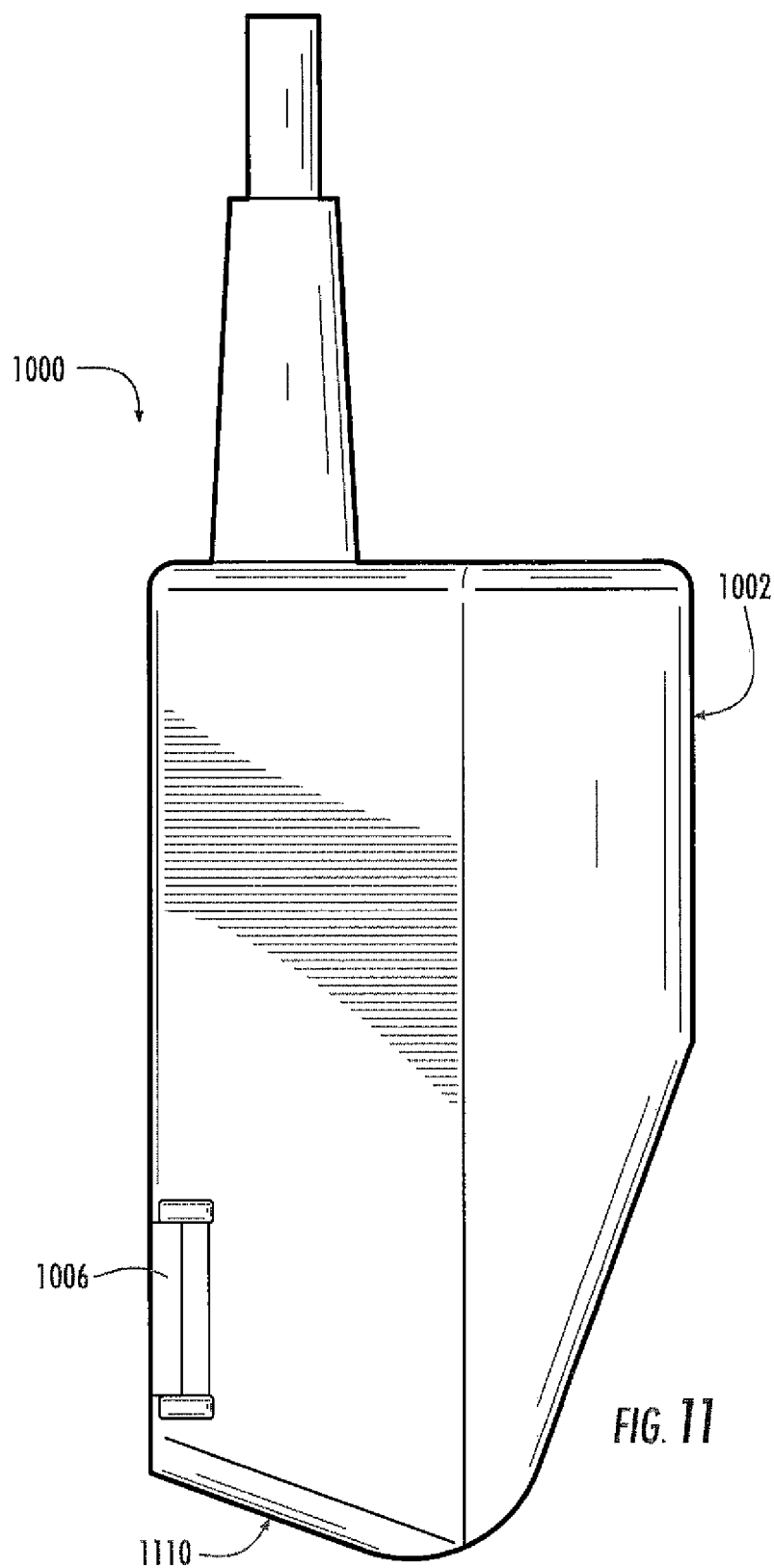
FIG. 11 is a side view of the probe device illustrated in FIG. 10.

Yet another embodiment is illustrated in FIG. 10. As can be seen according to this embodiment, a device 1000 need not include a separate handle portion. Such a device can be comfortably held by the rounded back portion 1002, with the angled skin contacting surface 1110 against a subject. A side view of device 1000 shown in FIG. 11 better illustrates the angle of skin contacting surface 1110.

Figure 12:
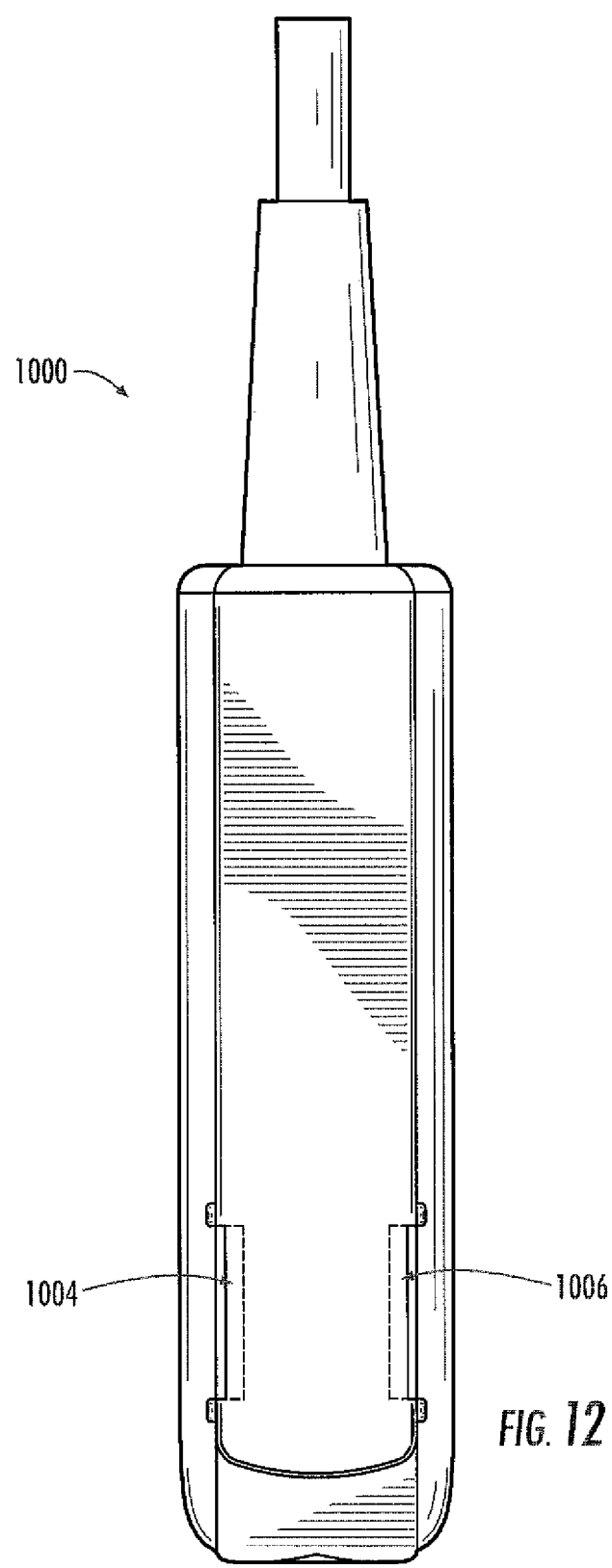
FIG. 12 is a front view of the probe device illustrated in FIG. 10.
Figure 13:
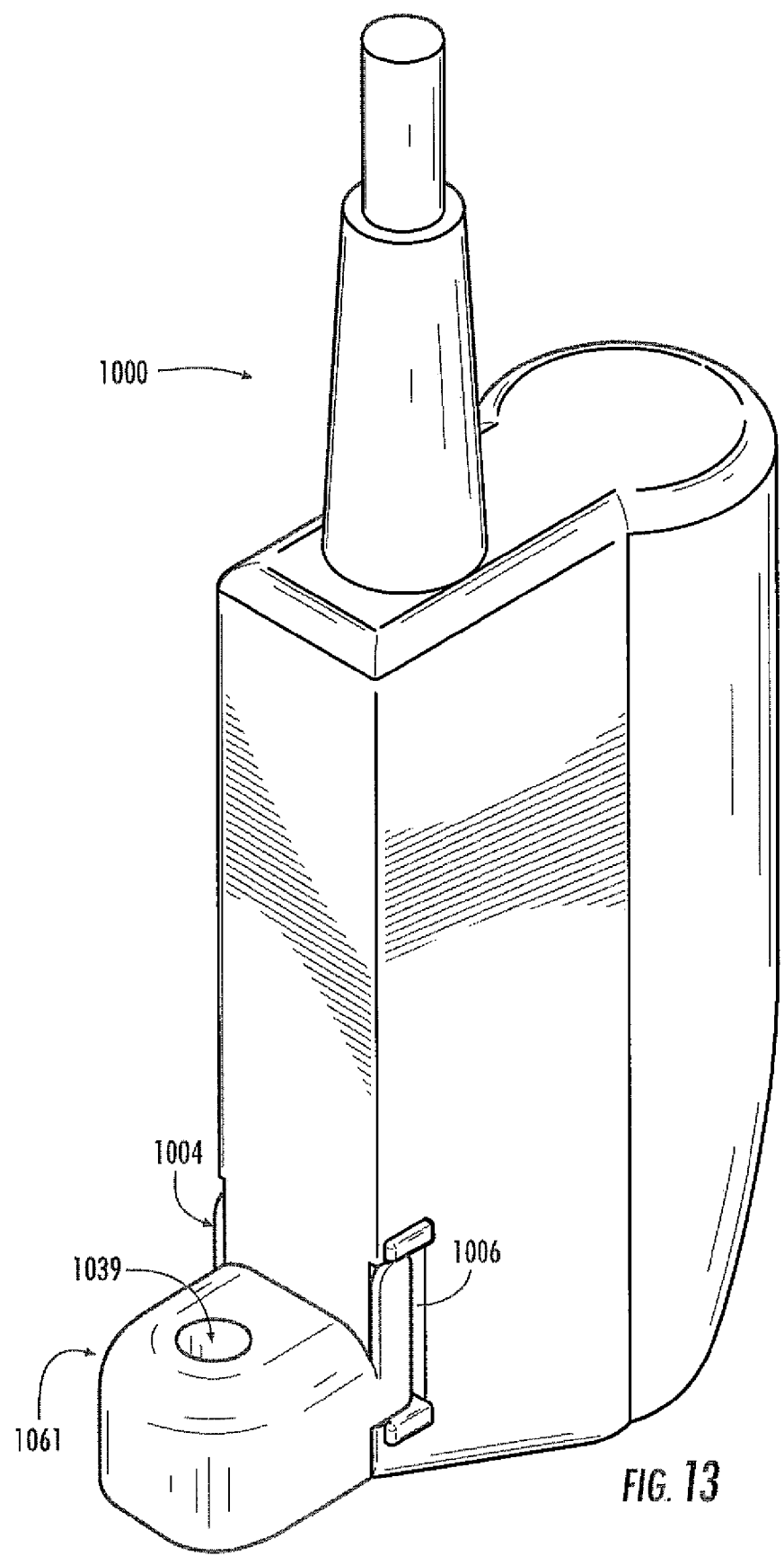
FIG. 13 illustrates the device of FIG. 10 including a removably attachable probe guide portion.
Figure 14:
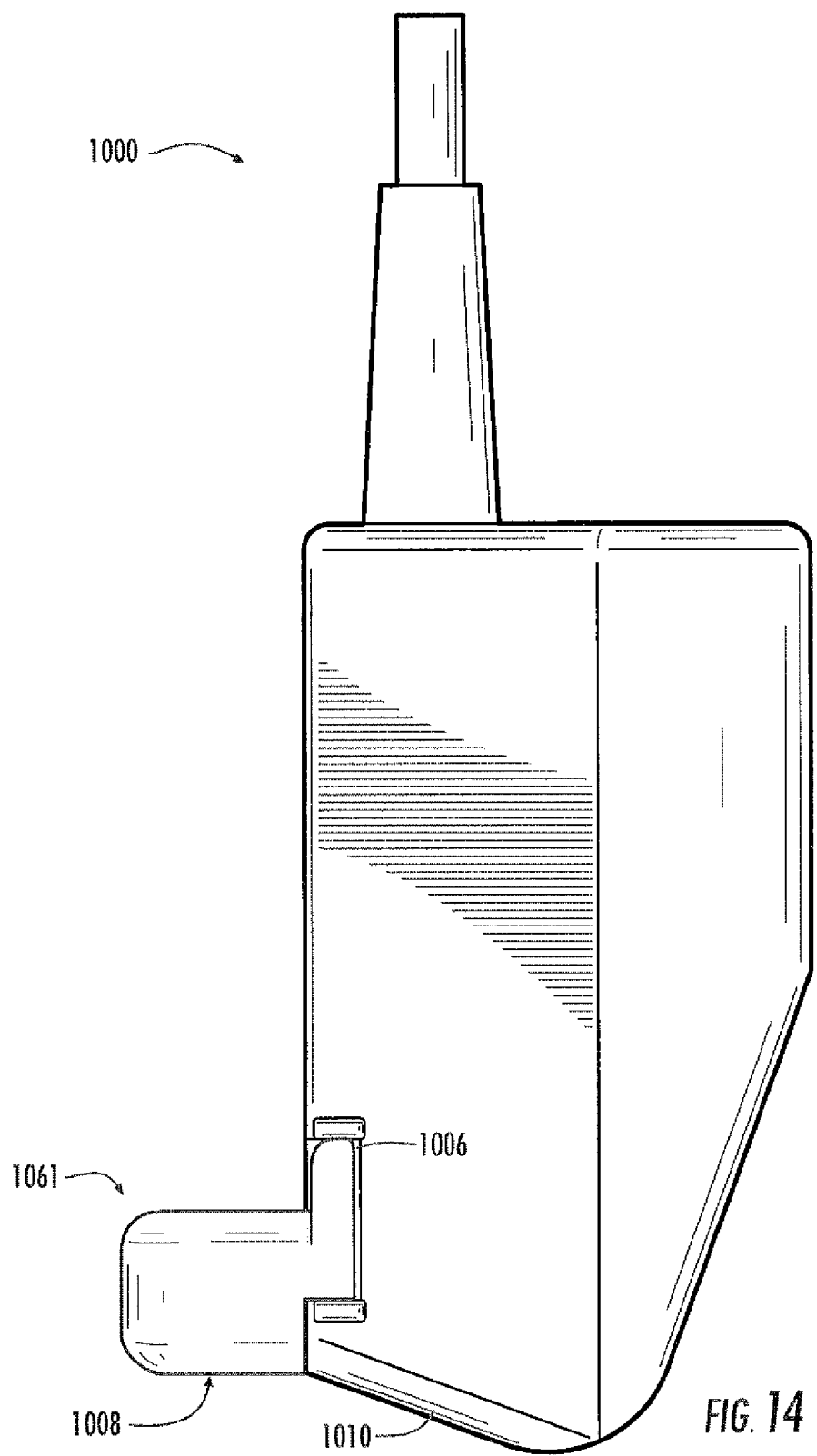
FIG. 14 is a side view of the device of FIG. 13.
Figure 15:
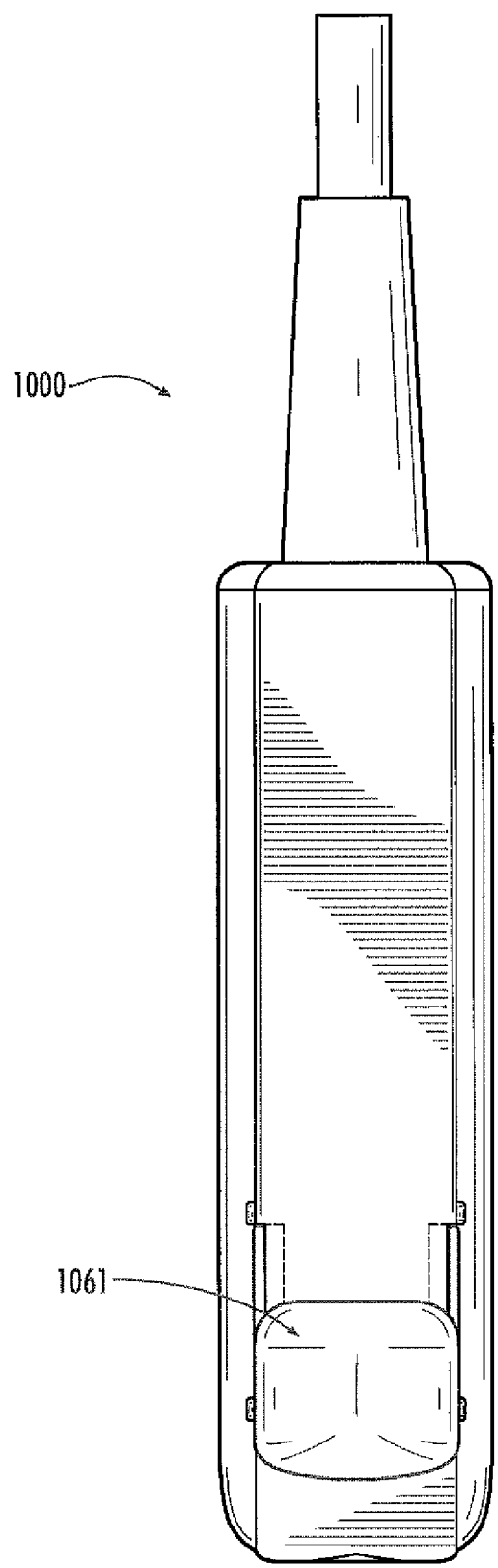
FIG. 15 is a front view of the device of FIG. 13.

A front view of device 1000 is shown in FIG. 12. As can be seen, device 1000 includes attachment slots 1004, 1006 on either side of the device. These attachment slots 1004, 1006 can be utilized to attach another portion of a device to device 1000. For example, FIG. 13 illustrates device 1000 including a probe guide portion 1061 attached to device 1000 via slots 1006. When attached, probe guide portion can, in one embodiment, be attached such that probe guide 1039 is aligned with an ultrasound transducer located in the base of device 1000. Of course, device 1000 need not include an ultrasound transducer in the base. FIG. 14 illustrates a side view of device 1000 including probe guide portion 1061 attached thereto. As can be seen, probe guide portion 1061 can define skin contacting surface 1008 and device 1000 can device skin contacting surface 1010, with the two surfaces 1008, 1010 held at an angle to one another to promote improved contact between a device and a subject, as previously discussed. FIG. 15 is a front view of the embodiment illustrated in FIGS. 13 and 14.

In one embodiment, a probe guide portion need not include a skin contacting surface. For instance, a separably removable probe guide portion can be attached to a device such that the base of the probe guide portion will be above and not contacting the skin of a subject. According to this embodiment, contact between a subject and a device will only be in the body of a device to which the probe guide portion is attached. For instance, when the body of a device incorporates an ultrasound transducer therein, the skin contacting surface can be at the ultrasound transducer surface, and the probe guide portion can be aligned with the transducer, and above the skin contacting surface of the body of the device.

Figure 16:
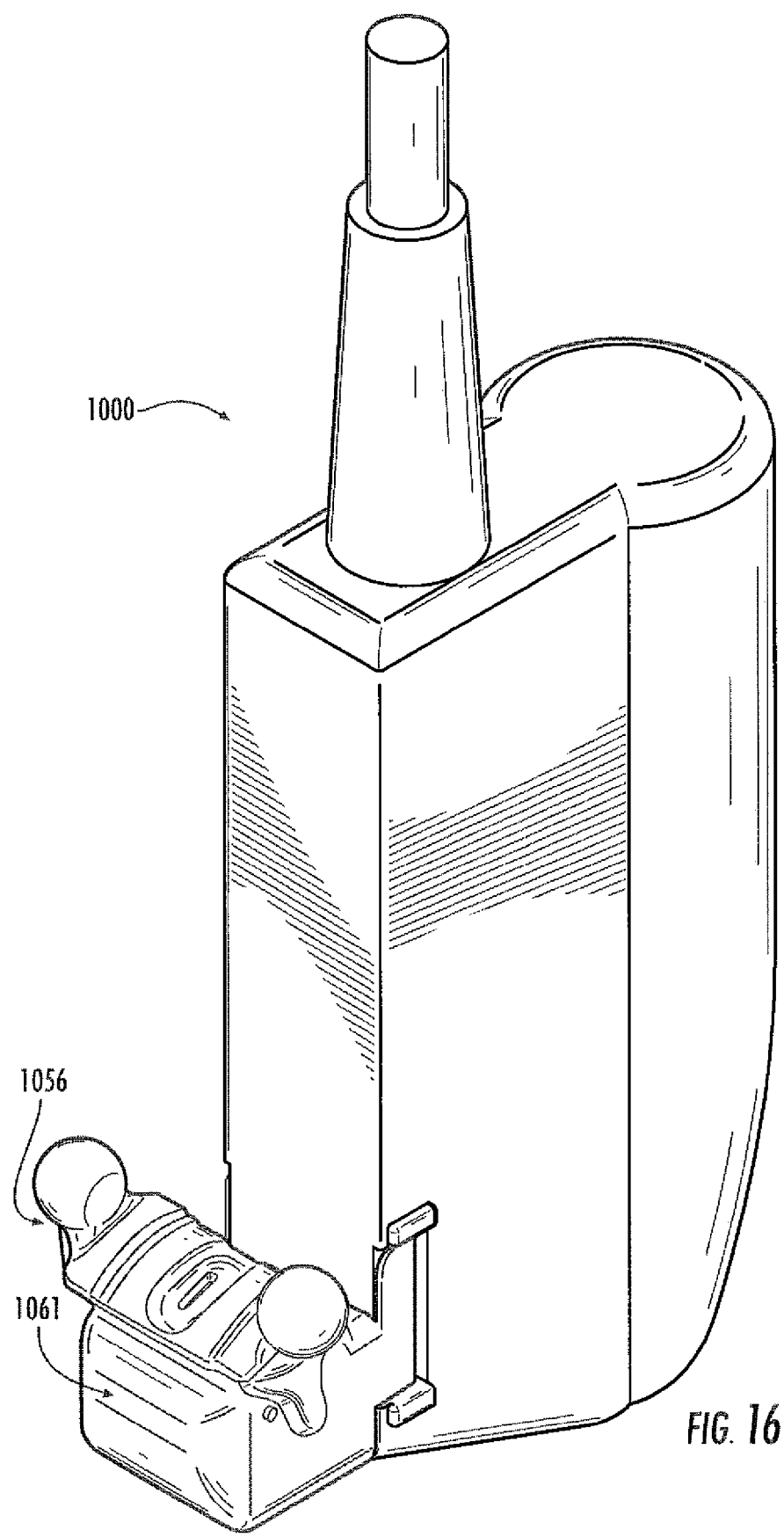
FIG. 16 illustrates the device of FIG. 13 with a clamp as described herein removably attached to the probe guide portion.
Figure 17:
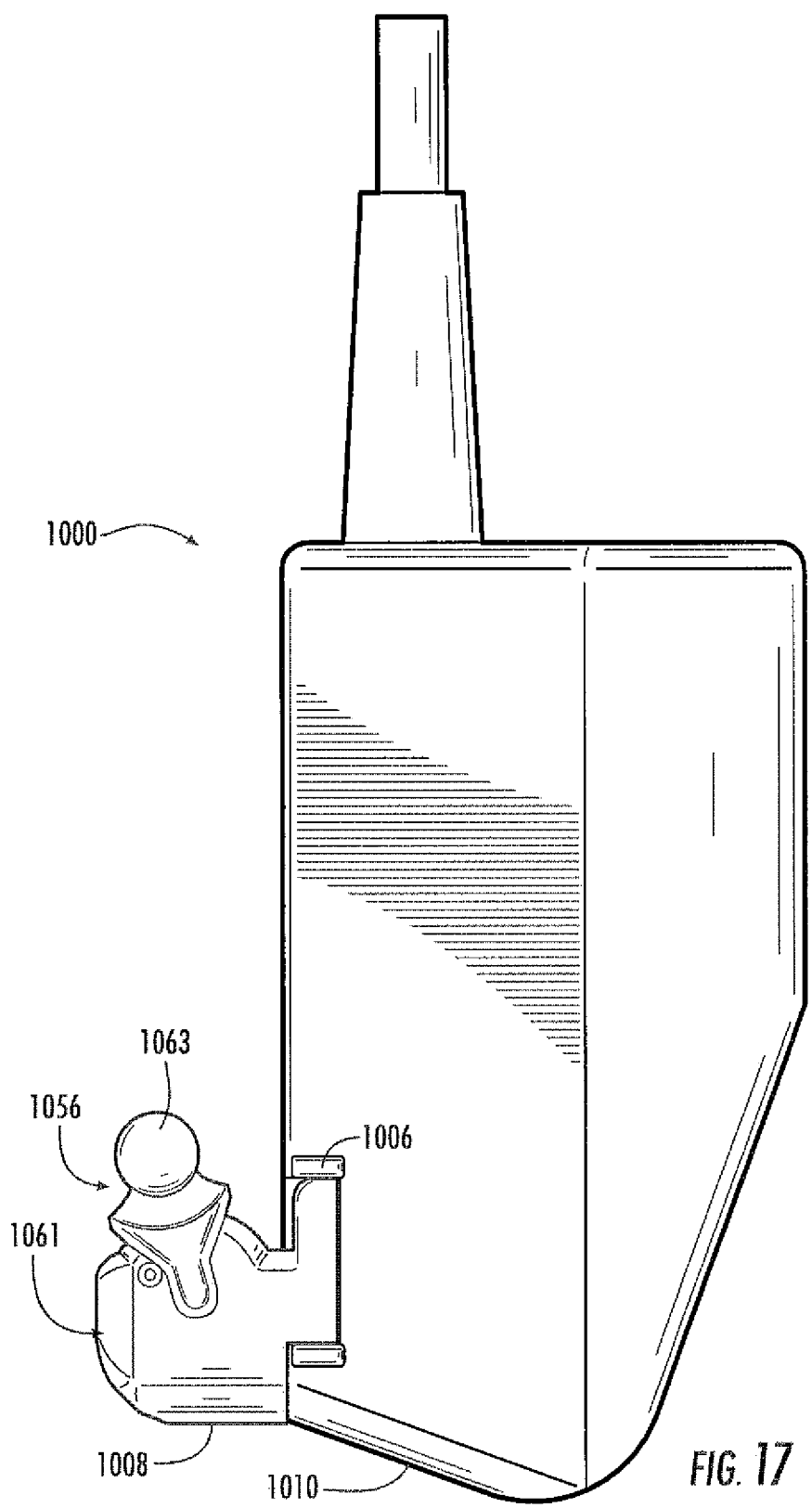
FIG. 17 is a side view of the device of FIG. 16
Figure 18:
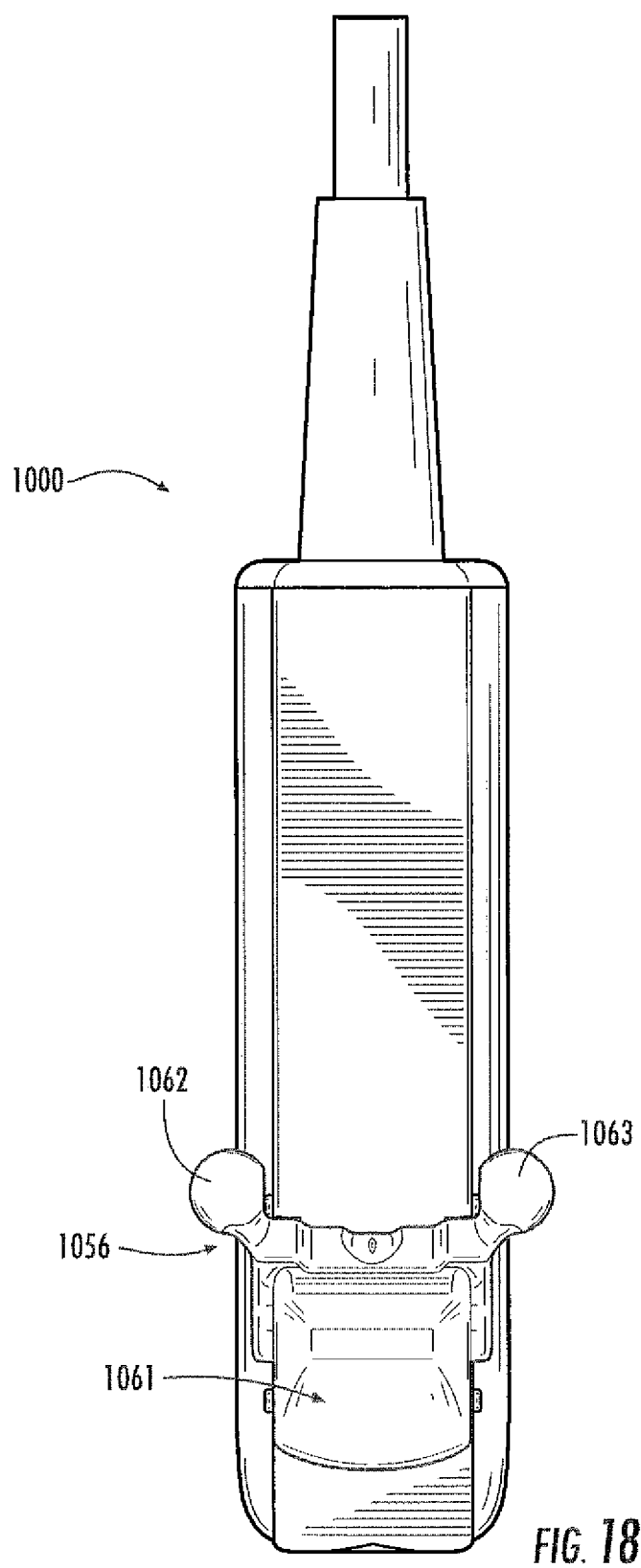
FIG. 18 is a front view of the device of FIG. 16.

FIG. 16 illustrates the device 1000 following attachment of a clamp 1056 to the probe guide portion 1061. FIG. 17 illustrates this embodiment in a side view and FIG. 18 illustrates this embodiment in a front view. During use, a device can be held against the skin and a probe can be passed through the probe guide. Upon reaching the desired subdermal location, the clamp 1056 can be activated, for instance by the user pulling formation 1063 from the unclamped to the clamped position.

Utilizing a probe device incorporating an ultrasound device, a probe tip can be guided to a percutaneous target that can be visualized on a scanned plane on a sonogram. For instance, the probe tip can travel on a path that defines a line that is coincident in the scanned plane, is parallel to the scanned plane, or intersects the scanned plane at a point. When utilizing the presently disclosed devices, the path of the probe to the target can be known, even if it cannot be discerned on the sonogram: the probe will advance toward the target on a straight line and at a predetermined angular relationship to the ultrasound housing base from the probe guide opening to the target that is imaged by the ultrasound. Thus, the path of the probe and the scanned plane of the sonogram image can both be defined by the orientation of the transducer and can be coordinated on the target. In order to strike the target, the probe can be merely guided along this known path the desired distance.

In an ideal situation, the probe itself can be visualized on the scanned plane. For instance, in those embodiments in which the path of the probe is on a line within the scanned plane, the probe can be seen in the sonogram, depending on the density of surrounding tissue and other process parameters. However, in one embodiment, even if the path of the probe is coincident with the scanned plane, the probe itself may not be visible on the sonogram, but artifacts of the passage of the probe can be visualized, e.g., shadows, motion of internal structures as the probe passes, and so forth.

In one preferred embodiment, the known path of the probe can be added to the sonogram, and the targeting procedures can be even further simplified. For example, one embodiment includes the addition of a targeting line on the sonogram extending from that point on the sonogram where the probe guide opening exits the housing (or enters the scanned plane) and projecting across the ultrasonic field in a straight line at the known angle. A targeting line can have any visual appearance. For instance, it can be a single thin line or a thick line roughly equivalent to the size of the probe. It can be a solid line representation or broken lines. In one embodiment, a targeting line can appear as two parallel lines set at a width up to the diameter of the probe. Any other visualizable conception of the term targeting line is encompassed herein.

Thus, if this targeting line is made to intersect the target that is imaged by the device, the operator can be confident that the probe is accurately directed to the target. In other embodiments, other targeting information can be displayed on the sonogram. For example, in one embodiment, information showing the approach of the probe to the target can be displayed.

In one particular embodiment, a motion detector can register motion of a probe in the probe guide, and that information can be displayed, for instance, as a real time virtual image of the probe on a sonogram. In this embodiment, the location of the probe tip in relation to the target and the moment when the probe tip strikes the target can be seen in real time by an operator watching the virtual probe on the monitor during the procedure.

FIG. 5 illustrates one embodiment of the disclosed subject matter wherein an image of a virtual probe may be overlaid on a sonogram. In this particular embodiment, the probe device can include a detector 170 located in the post of the sterilizable shield 230 or in the post of the transducer housing enclosed within the shield 230. Detector 170 can recognize and monitor the movement of probe 154 as it passes through the probe guide and into a subject. Information from detector 170 and the ultrasound transducer can pass through cable 124 to monitor 174. The probe 154 can then be imaged on a monitor 174 as virtual probe image 178. The monitor 174 can also show the internal target, for instance a blood vessel 176.

A variety of different possible detectors as are generally known in the art may be utilized as detector 170. For instance, detector 170 can utilize infrared (IR), ultrasound, optical, laser, magnetic or other motion detection mechanisms. In addition, the location of detector 170 is not critical to the invention. In the embodiment illustrated in FIG. 5, detector 170 is located in the post of either the shield 230 or the ultrasound transducer housing enclosed within the shield 230. In other embodiments, however, the detector may be located elsewhere in the system including, for example, on a portion of the probe itself.

Signals from detector 170 can create a data stream which can be sent to a processor. A processing unit can be internal or external to the hand-held device. For example, data from detector 170 can be sent to a standard lap top or desk top computer processor or part of a self-contained ultrasound system as is known in the art. A processor can be loaded with suitable recognition and analysis software and can receive and analyze the stream of data from detector 170. The processing unit can also include standard imaging software as is generally known in the art to receive data from the ultrasound transducer via cable 124. Probe 154 can be of a predetermined length which can be input data entered into a processor by the user or can be preprogrammed into the system as default data. Thus, through analysis of the data stream received from detector 170 and from ultrasound transducer 120, a processor can be programmed to calculate the relative position of the probe tip in relation to the ultrasound transducer 120, in relation to detector 170, in relation to the exit of the probe guide, or to any other convenient reference point. A processor can communicate this position information digitally to monitor 174 and the information can be displayed on the monitor such as in a numerical format or optionally as a real time image of a virtual probe 178 shown in conjunction with the sonogram including an image 176 of the target, such as a blood vessel.

In such a manner, disclosed devices can be utilized to actually show the approach of the probe toward the target on the monitor throughout the entire procedure. In addition disclosed devices can be utilized to ensure the probe tip remains at the target during subsequent procedures. For example, in those embodiments wherein a detector 170 monitors the motion of the probe 154, as long as the detector is interacting with the probe, e.g., the sending and receiving of signals between the two, the image 176 of probe 154 can remain on the monitor 174. Thus, any motion of the probe tip in relation to the target can be noted by an observer, even following the clamping of the probe 154 within the probe guide by use of clamp 156 as previously discussed.

Presently disclosed probe devices and methods may be utilized in many different medical procedures. Exemplary applications for the devices can include, without limitation Central Venous Catheterization
Cardiac Catheterization (Central Arterial Access)
Dialysis Catheter Placement
Breast Biopsies
Paracentesis
Pericardiocentesis
Thoracentesis
Arthrocentesis
Lumbar Puncture
Epidural Catheter Placement Peripherally Inserted Central Catheter (PICC) line placement
Thyroid Nodule Biopsies
Cholecystic Drain Placement
Amniocentesis
Regional Anesthesia—Nerve Block Some of these exemplary procedures have employed the use of ultrasound in the past, and all of these procedures, as well as others not specifically listed, could utilize disclosed probe devices to improve procedural safety as well as patient safety and comfort, in addition to provide more economical use of ultrasound devices.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A medical probe device comprising an ultrasound transducer, the medical probe device defining a probe guide therethrough, the probe guide defining a longitudinal axis and providing an unimpeded passageway through the medical probe device for passage of a probe therethrough, the medical probe device further comprising a clamp defining a clamping surface, at least a portion of the clamp being moveable from a first position to a second position and in a direction that crosses the longitudinal axis of the probe guide such that a probe is free to move in the probe guide when the clamp is at the first position and such that the clamping surface is in contact with a probe located in the probe guide when the clamp is at the second position, wherein the second position is a clamping position that prevents motion of a probe held in the probe guide.

2. The medical probe device of claim 1, wherein the clamp pivots about an axis from the first position to the second position.

3. The medical probe device of claim 1, wherein the clamp slides laterally over a surface of the base from the first position to the second position.

4. The medical probe device of claim 1, wherein the clamping surface is a surface of an aperture defined by the clamp.

5. The medical probe device of claim 4, wherein the aperture narrows in width from a first end to a second end.

6. The medical probe device of claim 1, further comprising a formation for moving the clamp from the first position to the second position.

7. The medical probe device of claim 1, the clamping surface defining a series of serrations.

8. The medical probe device of claim 1, wherein the ultrasound transducer is aligned with the probe guide.

9. The medical probe device of claim 1, wherein the path of a probe guided through the probe guide is within a scanned plane of a sonogram.

10. The medical probe device of claim 1, wherein the ultrasound transducer is removably cooperable with the probe guide.

11. The medical probe device of claim 1, further comprising a detector for detecting motion of a probe within the probe guide, the detector being in communication with a processing unit for displaying information concerning the motion of a probe in the probe guide.

12. The medical probe device of claim 11, wherein the information is displayed as a computer generated image of a virtual probe on the monitor.

13. The medical probe device of claim 11, wherein the detector utilizes a magnetic motion detection mechanism.

14. A medical probe device comprising an ultrasound transducer housing and a sterilizable shield removably cooperable with the ultrasound transducer housing, the sterilizable shield defining a probe guide, the probe guiding defining an axis and providing an unimpeded passageway through the sterilizable shield for passage of a probe therethrough, the medical probe device comprising a clamp defining a clamping surface, at least a portion of the clamp being moveable in a direction that crosses the axis of the probe guide from a first position to a second position such that a probe in the probe guide is free to move when the clamp is at the first position and such that the clamping surface is in contact with a probe in the probe guide when the clamp is at the second position, wherein the second position is a clamping position that prevents motion of a probe held in the probe guide.

15. The medical probe device of claim 14, wherein the probe guide of the sterilizable shield is adapted for receipt in a probe guide opening defined by the ultrasound transducer housing.

16. The medical probe device of claim 14, the sterilizable shield further comprising a first section, a second section, and a fastener for connecting the first section and the second section to one another.

17. The medical probe device of claim 16, wherein the fastener is a single-use fastener that is permanently disabled upon disconnection and separation of the first section and the second section from one another.

18. The medical probe device of claim 14, the sterilizable shield comprising a removably cooperable section that defines the probe guide therethrough.

19. The medical probe device of claim 14, further comprising a formation for moving the clamp from the first position to the second position.

20. The medical probe device of claim 14, wherein the ultrasound transducer is connectable to a monitor for displaying a sonogram.

21. The medical probe device of claim 20, further comprising a detector for detecting motion of a probe within the probe guide, the detector being in communication with a processing unit for displaying information concerning the motion of a probe in the probe guide.

22. The medical probe device of claim 21, wherein the information is displayed as a computer generated image of a virtual probe on the monitor.

23. The medical probe device of claim 21, wherein the detector utilizes a magnetic motion detection mechanism.

24. The medical probe device of claim 14, wherein the clamping surface is the surface of an aperture defined by the clamp.

25. A method for guiding a percutaneous probe to a percutaneous target comprising:
guiding a probe through the probe guide of a medical probe device to a predetermined percutaneous location, the medical probe device including a clamp, the probe guide defining an axis, the medical probe device further comprising an ultrasound transducer housing, the ultrasound transducer housing including an ultrasound transducer for transmitting an ultrasonic beam and receiving reflections of the ultrasonic beam; and selectively moving at least a portion of the clamp across the axis of the probe guide from a first position to a second position when the probe is at the predetermined location, wherein the probe is free to move in the probe guide when the clamp is at the first position and a clamping surface defined by the clamp contacts the probe when the clamp is at the second position, said contact preventing motion of the probe held in the probe guide.

26. The method according to claim 25, wherein the clamping surface deforms around a portion of the probe when the clamp is at the second position.

27. The method according to claim 25, wherein the clamping surface cuts into the side of the probe when the clamp is at the second position.

28. The method according to claim 25, wherein two clamping surfaces defined by the clamp contact the probe when the clamp is at the second position.

29. The method according to claim 25, wherein the probe contacts the clamping surface and a wall of the probe guide when the clamp is at the second position.

30. The method according to claim 25, the medical probe device comprising a sterilizable shield, the method further comprising locating the ultrasound transducer housing within the sterilizable shield.

31. The method according to claim 30, the ultrasound transducer housing defining a probe guide opening therethrough, the sterilizable shield defining the probe guide, the method further comprising receiving the probe guide opening within the probe guide.

32. The method according to claim 30, the sterilizable shield defining the probe guide.

33. The method of claim 25, the method further comprising forming a sonogram of the percutaneous location on a monitor in response to the reflections of the ultrasonic beam.

34. The method of claim 33, further comprising:
creating a data stream in response to motion of the probe in the probe guide; and
forming a real time image of information contained in the data stream.

35. The method of claim 34, wherein the real time image is an image of a virtual probe overlaid on the sonogram.

36. The method of claim 34, further comprising detecting the motion of the probe in the probe guide through utilization of a magnetic motion detection mechanism.

37. The method of claim 33, wherein the percutaneous location is the lumen of a blood vessel.

38. The method of claim 25, wherein the method is carried out by a single operator.

39. The method of claim 25, the method further comprising releasing the ultrasound transducer housing from the sterilizable shield, wherein a fastener of the sterilizable shield is permanently disabled upon release of the ultrasound transducer housing from the sterilizable shield.

* * * * *